United States Patent
Bent et al.

(10) Patent No.: US 11,821,035 B1
(45) Date of Patent: Nov. 21, 2023

(54) COMPOSITIONS AND METHODS OF MAKING GENE EXPRESSION LIBRARIES

(71) Applicant: 10x Genomics, Inc., Pleasanton, CA (US)

(72) Inventors: Zachary Bent, Pleasanton, CA (US); Marlon Stoeckius, Stockholm (SE)

(73) Assignee: 10x Genomics, Inc., Pleasanton, CA (US)

( * ) Notice: Subject to any disclaimer, the term of this patent is extended or adjusted under 35 U.S.C. 154(b) by 171 days.

(21) Appl. No.: 17/162,991

(22) Filed: Jan. 29, 2021

Related U.S. Application Data

(60) Provisional application No. 63/033,566, filed on Jun. 2, 2020, provisional application No. 62/967,361, filed on Jan. 29, 2020.

(51) Int. Cl.
    *C12Q 1/6876* (2018.01)

(52) U.S. Cl.
    CPC .................................. *C12Q 1/6876* (2013.01)

(58) Field of Classification Search
    None
    See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,883,867 A | 11/1989 | Lee | |
| 4,965,188 A | 10/1990 | Mullis | |
| 5,002,882 A | 3/1991 | Lunnen | |
| 5,130,238 A | 7/1992 | Malek | |
| 5,308,751 A | 5/1994 | Ohkawa | |
| 5,321,130 A | 6/1994 | Yue | |
| 5,410,030 A | 4/1995 | Yue | |
| 5,436,134 A | 7/1995 | Haugland | |
| 5,455,166 A | 10/1995 | Walker | |
| 5,472,881 A | 12/1995 | Beebe et al. | |
| 5,494,810 A | 2/1996 | Barany et al. | |
| 5,503,980 A | 4/1996 | Cantor | |
| 5,512,439 A | 4/1996 | Hornes | |
| 5,512,462 A | 4/1996 | Cheng | |
| 5,582,977 A | 12/1996 | Yue | |
| 5,599,675 A | 2/1997 | Brenner | |
| 5,610,287 A | 3/1997 | Nikiforov et al. | |
| 5,641,658 A | 6/1997 | Adams | |
| 5,648,245 A | 7/1997 | Fire et al. | |
| 5,658,751 A | 8/1997 | Yue | |
| 5,750,341 A | 5/1998 | Macevicz | |
| 5,763,175 A | 6/1998 | Brenner | |
| 5,807,522 A | 9/1998 | Brown et al. | |
| 5,830,711 A | 11/1998 | Barany et al. | |
| 5,837,832 A | 11/1998 | Chee et al. | |
| 5,837,860 A | 11/1998 | Anderson et al. | |
| 5,854,033 A | 12/1998 | Lizardi | |
| 5,863,753 A | 1/1999 | Haugland | |
| 5,871,921 A | 2/1999 | Landegren et al. | |
| 5,912,148 A | 6/1999 | Eggerding | |
| 5,919,626 A | 7/1999 | Shi et al. | |
| 6,013,440 A | 1/2000 | Lipshutz | |
| 6,027,889 A | 2/2000 | Barany et al. | |
| 6,060,240 A | 5/2000 | Kamb et al. | |
| 6,130,073 A | 10/2000 | Eggerding | |
| 6,143,496 A | 11/2000 | Brown | |
| 6,153,389 A | 11/2000 | Haarer | |
| 6,165,714 A | 12/2000 | Lane et al. | |
| 6,172,218 B1 | 1/2001 | Brenner | |
| 6,210,891 B1 | 4/2001 | Nyren | |
| 6,210,894 B1 | 4/2001 | Brennan | |
| 6,214,587 B1 | 4/2001 | Dattagupta | |
| 6,258,568 B1 | 7/2001 | Nyren | |
| 6,266,459 B1 | 7/2001 | Walt | |
| 6,274,320 B1 | 8/2001 | Rothberg | |
| 6,300,063 B1 | 10/2001 | Lipshutz et al. | |
| 6,309,824 B1 | 10/2001 | Drmanac | |
| 6,344,316 B1 | 2/2002 | Lockhart | |
| 6,355,431 B1 | 3/2002 | Chee | |
| 6,368,801 B1 | 4/2002 | Faruqi | |
| 6,391,937 B1 | 5/2002 | Beuhler et al. | |
| 6,401,267 B1 | 6/2002 | Drmanac | |
| 6,404,907 B1 | 6/2002 | Gilchrist | |
| 6,432,360 B1 | 8/2002 | Church et al. | |
| 6,503,713 B1 | 1/2003 | Rana | |
| 6,506,561 B1 | 1/2003 | Cheval et al. | |
| 6,544,732 B1 | 4/2003 | Chee | |
| 6,620,584 B1 | 9/2003 | Chee | |
| 6,632,641 B1 | 10/2003 | Brennan | |
| 6,699,710 B1 | 3/2004 | Kononen | |
| 6,737,236 B1 | 5/2004 | Pieken et al. | |

(Continued)

FOREIGN PATENT DOCUMENTS

| CN | 1680604 | 10/2005 |
|---|---|---|
| EP | 1910562 | 4/2008 |

(Continued)

OTHER PUBLICATIONS

[No Author Listed], "Chromium Next GEM Single Cell 3' Reagent Kits v3.1 (Dual Index)—User Guide," 10x Genomics, Mar. 2021, Document No. CG000315, 61 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.

(Continued)

*Primary Examiner* — Amanda Haney
(74) *Attorney, Agent, or Firm* — Fish & Richardson P.C.

(57) ABSTRACT

Provided herein are methods of detecting target nucleic acids and uses of the same.

20 Claims, 12 Drawing Sheets
Specification includes a Sequence Listing.

(56) References Cited

U.S. PATENT DOCUMENTS

| | | |
|---|---|---|
| 6,770,441 B2 | 8/2004 | Dickinson |
| 6,773,886 B2 | 8/2004 | Kaufman |
| 6,787,308 B2 | 9/2004 | Balasubramanian |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,859,570 B2 | 2/2005 | Walt |
| 6,864,052 B1 | 3/2005 | Drmanac |
| 6,890,741 B2 | 5/2005 | Fan et al. |
| 6,897,023 B2 | 5/2005 | Fu |
| 6,942,968 B1 | 9/2005 | Dickinson et al. |
| 7,057,026 B2 | 6/2006 | Barnes |
| 7,115,400 B1 | 10/2006 | Adessi |
| 7,118,883 B2 | 10/2006 | Inoue |
| 7,166,431 B2 | 1/2007 | Chee et al. |
| 7,211,414 B2 | 5/2007 | Hardin |
| 7,255,994 B2 | 8/2007 | Lao |
| 7,258,976 B2 | 8/2007 | Mitsuhashi |
| 7,259,258 B2 | 8/2007 | Kozlov et al. |
| 7,297,518 B2 | 11/2007 | Quake |
| 7,315,019 B2 | 1/2008 | Turner |
| 7,329,492 B2 | 2/2008 | Hardin |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,427,678 B2 | 9/2008 | Pieken et al. |
| 7,537,897 B2 | 5/2009 | Brenner |
| 7,563,576 B2 | 7/2009 | Chee |
| 7,582,420 B2 | 9/2009 | Oliphant et al. |
| 7,601,492 B2 | 10/2009 | Fu et al. |
| 7,601,498 B2 | 10/2009 | Mao |
| 7,611,869 B2 | 11/2009 | Fan |
| 7,635,566 B2 | 12/2009 | Brenner |
| 7,674,752 B2 | 3/2010 | He |
| 7,709,198 B2 | 5/2010 | Luo et al. |
| 7,754,429 B2 | 7/2010 | Rigatti |
| 7,776,567 B2 | 8/2010 | Mao |
| 7,803,943 B2 | 9/2010 | Mao |
| 7,844,940 B2 | 11/2010 | Shin et al. |
| 7,910,304 B2 | 3/2011 | Drmanac |
| 7,955,794 B2 | 6/2011 | Shen et al. |
| 7,960,119 B2 | 6/2011 | Chee |
| 7,960,120 B2 | 6/2011 | Rigatti |
| 8,003,354 B2 | 8/2011 | Shen et al. |
| 8,030,477 B2 | 10/2011 | Cerrina et al. |
| 8,076,063 B2 | 12/2011 | Fan |
| 8,148,068 B2 | 4/2012 | Brenner |
| 8,198,028 B2 | 6/2012 | Rigatti et al. |
| 8,206,917 B2 | 6/2012 | Chee |
| 8,288,103 B2 | 10/2012 | Oliphant |
| 8,460,865 B2 | 6/2013 | Chee |
| 8,481,257 B2 | 7/2013 | Van Eijk |
| 8,486,625 B2 | 7/2013 | Gunderson |
| 8,586,310 B2 | 11/2013 | Mitra |
| 8,603,743 B2 | 12/2013 | Liu et al. |
| 8,604,182 B2 | 12/2013 | Luo et al. |
| 8,685,889 B2 | 4/2014 | Van Eijk |
| 8,778,849 B2 | 7/2014 | Bowen |
| 8,785,353 B2 | 7/2014 | Van Eijk |
| 8,815,512 B2 | 8/2014 | Van Eijk |
| 8,835,358 B2 | 9/2014 | Fodor |
| 8,895,249 B2 | 11/2014 | Shen |
| 8,911,945 B2 | 12/2014 | Van Eijk |
| 8,936,912 B2 | 1/2015 | Mitra |
| 8,951,726 B2 | 2/2015 | Luo et al. |
| 9,023,768 B2 | 5/2015 | Van Eijk |
| 9,062,348 B1 | 6/2015 | Van Eijk |
| 9,080,210 B2 | 7/2015 | Van Eijk |
| 9,085,798 B2 | 7/2015 | Chee |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,376,716 B2 | 6/2016 | Van Eijk |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,593,365 B2 | 3/2017 | Frisen et al. |
| 9,644,204 B2 | 5/2017 | Hindson et al. |
| 9,694,361 B2 | 7/2017 | Bharadwaj |
| 9,702,004 B2 | 7/2017 | Van Eijk |
| 9,727,810 B2 | 8/2017 | Fodor et al. |
| 9,777,324 B2 | 10/2017 | Van Eijk |
| 9,783,841 B2 | 10/2017 | Nolan et al. |
| 9,834,814 B2 | 12/2017 | Peter et al. |
| 9,850,536 B2 | 12/2017 | Oliphant et al. |
| 9,868,979 B2 | 1/2018 | Chee et al. |
| 9,879,313 B2 | 1/2018 | Chee et al. |
| 9,889,422 B2 | 2/2018 | Smith et al. |
| 9,896,721 B2 | 2/2018 | Van Eijk |
| 9,898,576 B2 | 2/2018 | Van Eijk |
| 9,898,577 B2 | 2/2018 | Van Eijk |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,990 B2 | 8/2018 | Boyden et al. |
| 10,095,832 B2 | 10/2018 | Van Eijk |
| 10,138,509 B2 | 11/2018 | Church et al. |
| 10,144,966 B2 | 12/2018 | Cantor |
| 10,208,982 B2 | 2/2019 | Bannish et al. |
| 10,273,541 B2 | 4/2019 | Hindson et al. |
| 10,308,982 B2 | 6/2019 | Chee |
| 10,357,771 B2 | 7/2019 | Bharadwaj |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,590,244 B2 | 3/2020 | Delaney et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |

(56) References Cited

U.S. PATENT DOCUMENTS

| | | |
|---|---|---|
| 11,519,022 B2 | 12/2022 | Chee |
| 11,519,033 B2 | 12/2022 | Schnall-Levin et al. |
| 11,519,138 B2 | 12/2022 | Meier et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 2002/0040275 A1 | 4/2002 | Cravatt |
| 2002/0137031 A1 | 9/2002 | Wolber |
| 2002/0164611 A1 | 11/2002 | Bamdad |
| 2002/0168645 A1 | 11/2002 | Taylor |
| 2003/0017451 A1 | 1/2003 | Wang et al. |
| 2003/0022207 A1 | 1/2003 | Balasubramanian |
| 2003/0040035 A1 | 2/2003 | Slamon |
| 2003/0064398 A1 | 4/2003 | Barnes |
| 2003/0073086 A1 | 4/2003 | Guire et al. |
| 2003/0148335 A1 | 8/2003 | Shen et al. |
| 2003/0162216 A1 | 8/2003 | Gold |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0224326 A1 | 11/2004 | Kim et al. |
| 2005/0037393 A1 | 2/2005 | Gunderson et al. |
| 2005/0048580 A1 | 3/2005 | Labaer |
| 2005/0100900 A1 | 5/2005 | Kawashima et al. |
| 2005/0130173 A1 | 6/2005 | Leamon et al. |
| 2005/0130188 A1 | 6/2005 | Walt |
| 2005/0136414 A1 | 6/2005 | Gunderson et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0244850 A1 | 11/2005 | Huang |
| 2005/0260653 A1 | 11/2005 | LaBaer |
| 2006/0199183 A1 | 9/2006 | Valat et al. |
| 2006/0199207 A1 | 9/2006 | Matysiak |
| 2006/0211001 A1 | 9/2006 | Yu et al. |
| 2006/0216775 A1 | 9/2006 | Burkart et al. |
| 2006/0263789 A1 | 11/2006 | Kincaid |
| 2006/0275799 A1 | 12/2006 | Banerjee et al. |
| 2007/0020640 A1 | 1/2007 | McCloskey et al. |
| 2007/0054288 A1 | 3/2007 | Su et al. |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0172873 A1 | 7/2007 | Brenner et al. |
| 2007/0207482 A1 | 9/2007 | Church et al. |
| 2007/0231823 A1 | 10/2007 | McKernan |
| 2007/0254305 A1 | 11/2007 | Paik et al. |
| 2007/0264656 A1 | 11/2007 | Kawamura |
| 2007/0269805 A1 | 11/2007 | Hogers |
| 2008/0009420 A1 | 1/2008 | Schroth et al. |
| 2008/0032301 A1 | 2/2008 | Rank et al. |
| 2008/0108804 A1 | 5/2008 | Hayashizaki et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0062148 A1 | 3/2009 | Goldberg |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0233802 A1 | 9/2009 | Bignell et al. |
| 2009/0253581 A1 | 10/2009 | van Eijk et al. |
| 2009/0291854 A1 | 11/2009 | Weisinger-Mayr et al. |
| 2009/0312193 A1 | 12/2009 | Kim et al. |
| 2010/0009871 A1 | 1/2010 | Reed et al. |
| 2010/0035249 A1 | 2/2010 | Hayashizaki et al. |
| 2010/0055733 A1 | 3/2010 | Lutolf et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0151464 A1 | 6/2010 | Stuelpnagel et al. |
| 2010/0184614 A1 | 7/2010 | Ye et al. |
| 2011/0024511 A1 | 2/2011 | Rietzler et al. |
| 2011/0028685 A1 | 2/2011 | Purkayastha et al. |
| 2011/0059436 A1 | 3/2011 | Hardin et al. |
| 2011/0059865 A1 | 3/2011 | Smith et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0275077 A1 | 11/2011 | James |
| 2012/0065081 A1 | 3/2012 | Chee |
| 2012/0129248 A1 | 5/2012 | Chee et al. |
| 2012/0135871 A1 | 5/2012 | van Eijk et al. |
| 2012/0156728 A1 | 6/2012 | Li et al. |
| 2012/0157322 A1 | 6/2012 | Myllykangas |
| 2012/0202698 A1 | 8/2012 | van Eijk et al. |
| 2012/0270748 A1 | 10/2012 | Chee et al. |
| 2013/0065788 A1 | 3/2013 | Glezer et al. |
| 2013/0096033 A1 | 4/2013 | Routenberg |
| 2013/0109595 A1 | 5/2013 | Routenberg |
| 2013/0171621 A1 | 7/2013 | Luo et al. |
| 2013/0261019 A1 | 10/2013 | Lin et al. |
| 2014/0066318 A1 | 3/2014 | Frisen et al. |
| 2014/0243224 A1 | 8/2014 | Barnard et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0378345 A1 | 12/2014 | Hindson et al. |
| 2015/0000854 A1 | 1/2015 | Gann-Fetter et al. |
| 2015/0005447 A1 | 1/2015 | Berti et al. |
| 2015/0087027 A1 | 3/2015 | Makarov et al. |
| 2015/0246336 A1 | 9/2015 | Somoza et al. |
| 2015/0292988 A1 | 10/2015 | Bharadwaj et al. |
| 2015/0344942 A1 | 12/2015 | Frisen et al. |
| 2015/0376609 A1 | 12/2015 | Hindson et al. |
| 2016/0024576 A1 | 1/2016 | Chee |
| 2016/0108458 A1 | 4/2016 | Frei et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0333403 A1 | 11/2016 | Chee |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0220733 A1 | 8/2017 | Zhuang et al. |
| 2017/0241911 A1 | 8/2017 | Rockel et al. |
| 2018/0051322 A1 | 2/2018 | Church et al. |
| 2018/0057873 A1 | 3/2018 | Zhou et al. |
| 2018/0105808 A1 | 4/2018 | Mikkelsen et al. |
| 2018/0112261 A1 | 4/2018 | Van Driel et al. |
| 2018/0201980 A1 | 7/2018 | Chee et al. |

(56) References Cited

U.S. PATENT DOCUMENTS

| | | |
|---|---|---|
| 2018/0216161 A1 | 8/2018 | Chen et al. |
| 2018/0216162 A1 | 8/2018 | Belhocine et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |
| 2018/0305681 A1 | 10/2018 | Jovanovich et al. |
| 2019/0017106 A1 | 1/2019 | Frisen et al. |
| 2019/0024153 A1 | 1/2019 | Frisen et al. |
| 2019/0024154 A1 | 1/2019 | Frisen et al. |
| 2019/0055594 A1 | 2/2019 | Samusik et al. |
| 2019/0064173 A1 | 2/2019 | Bharadwaj et al. |
| 2019/0085383 A1 | 3/2019 | Church et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 * | 7/2019 | Frisén ................. C12Q 1/6834 |
| 2019/0233878 A1 | 8/2019 | Delaney et al. |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0224244 A1 | 7/2020 | Nilsson et al. |
| 2020/0239946 A1 | 7/2020 | Dewal |
| 2020/0256867 A1 | 8/2020 | Hennek et al. |
| 2020/0277663 A1 | 9/2020 | Iver |
| 2020/0277664 A1 | 9/2020 | Frenz |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |

(56) References Cited

U.S. PATENT DOCUMENTS

| | | |
|---|---|---|
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |

FOREIGN PATENT DOCUMENTS

| | | |
|---|---|---|
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 1999/044062 | 9/1999 |
| WO | WO 1999/044063 | 9/1999 |
| WO | WO 2001/007915 | 2/2001 |
| WO | WO 2002/059355 | 8/2002 |
| WO | WO 2002/077283 | 10/2002 |
| WO | WO 2003/002979 | 1/2003 |
| WO | WO 2003/010176 | 2/2003 |
| WO | WO 2005/007814 | 1/2005 |
| WO | WO 2005/042759 | 5/2005 |
| WO | WO 2005/065814 | 7/2005 |
| WO | WO 2007/073171 | 6/2007 |
| WO | WO 2007/076726 | 7/2007 |
| WO | WO 2007/145612 | 12/2007 |
| WO | WO 2008/022332 | 2/2008 |
| WO | WO 2009/032167 | 3/2009 |
| WO | WO 2009/152928 | 12/2009 |
| WO | WO 2010/126614 | 11/2010 |
| WO | WO 2011/014879 | 2/2011 |
| WO | WO 2011/068088 | 6/2011 |
| WO | WO 2011/071943 | 6/2011 |
| WO | WO 2011/127099 | 10/2011 |
| WO | WO 2012/140224 | 10/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/150082 | 10/2013 |
| WO | WO 2013/150083 | 10/2013 |
| WO | WO 2014/060483 | 4/2014 |
| WO | WO 2014/163886 | 10/2014 |
| WO | WO 2014/210223 | 12/2014 |
| WO | WO 2014/210225 | 12/2014 |
| WO | WO 2015/085275 | 6/2015 |
| WO | WO 2016/126882 | 8/2016 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/075293 | 5/2017 |
| WO | WO 2017/096158 | 7/2017 |
| WO | WO 2018/064640 | 4/2018 |
| WO | WO 2018/091676 | 5/2018 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047007 | 3/2020 |
| WO | WO 2020/047010 | 3/2020 |
| WO | WO 2020/053655 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |

(56) References Cited

FOREIGN PATENT DOCUMENTS

| WO | WO 2022/271820 | 12/2022 |
|----|----|----|
| WO | WO 2023/287765 | 1/2023 |
| WO | WO 2023/018799 | 2/2023 |
| WO | WO 2023/034489 | 3/2023 |

OTHER PUBLICATIONS

Czarnik, "Encoding methods for combinatorial chemistry," Curr Opin Chem Biol., Jun. 1997, 1(1):60-6.
MacBeath et al., "Printing proteins as microarrays for high-throughput function determination," Science, Sep. 2000, 289(5485):1760-1763.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564ceb96bc294967/CG000238_VisiumSpatialTissueOptimizationUserGuide_Rev_A.pdf>, 46 pages.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
[No Author Listed], "Chromium Next GEM Single Cell 3' Reagent Kits v3.1—User Guide," 10x Genomics, Document No. CG000204, Nov. 2019, 58 pages.
[No Author Listed]. "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_ UserGuide_RevD.pdf>, 69 pages.
10xGenomics.com, [online],"Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.
Adessi et al., "Solid phase DNA amplification: characterisation of primer attachment and amplification mechanisms," Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Agbavwe et al., "Efficiency, error and yield in light-directed maskless synthesis of DNA microarrays," Journal of Nanobiotechnology, Dec. 2011, 9:57, 17 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Andresen et al., "Deciphering the Antibodyome-Peptide Arrays for Serum Antibody Biomarker Diagnostics," Current Proteomics, 6(1):1-12, 2009.
Armani et al, "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Beier et al., "Versatile derivatisation of solid support media for covalent bonding on DNA-microchips," Nucleic Acids Res., May 1999, 27(9):1970-7.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration; structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chatterjee et al., "Protein Microarray On-Demand: A Novel Protein Microarray System," PLos One, 2008, 3(9):e3265, 5 pages.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "µCB-seq: microfluidic cell barcoding and sequencing for high-resolution imaging and sequencing of single cells," Lab Chip, Nov. 2020, 20(21):3899-3913.
Cheng et al., "Sensitive Detection of Small Molecules by Competitive Immunomagnetic-Proximity Ligation Assay," Anal Chem, 2012, 84:2129-2132.

(56) References Cited

OTHER PUBLICATIONS

Chrisey et al., "Covalent attachment of synthetic DNA to self-assembled monolayer films," Nucleic Acids Res., Aug. 1996, 24(15):3031-9.
Condina et al., "A sensitive magnetic bead method for the detection and identification of tyrosine phosphorylation in proteins by MALDI-TOF/TOF MS," Proteomics, 2009, 9:3047-3057.
Constantine et al.. "Use of genechip high-density oligonucleotide arrays for gene expression monitoring," Life Sceience News, Amersham Life Science, 1998, pp. 11-14.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015. 16(1):57-66.
Dahl et al., "Circle-to-circle amplification for precise and sensitive DNA analysis," Proc. Natl. Acad. Sci., 2004, 101(13):4548-4553.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dean et al., "Comprehensive human genome amplification using multiple displacement amplification," Proc Natl. Acad. Sci. USA, 2002, 99(8):5261-66.
Drmanac et al., "Accurate sequencing by hybridization for DNA diagnostics and individual genomics," Nature Biotechnology, 16:54-58, 1998.
Duncan et al., "Affinity chromatography of a sequence-specific DNA binding protein using Teflon-linked oligonucleotides," Anal. Biochem., 1988, 169(1):104-108.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Fire et al., "Rolling replication of short DNA circles," Proc. Natl. Acad. Sci., 1995, 92(10):4641-4645.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Gracia Villacampa et al., "Genome-wide Spatial Expression Profiling in FFPE Tissues," bioRxiv, 2020, pp. 38 pages.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hayes et al., "Electrophoresis of proteins and nucleic acids: I—Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Hölz et al., "High-Efficiency Reverse (5'→3') Synthesis of Complex DNA Microarrays," Scientific Reports, Oct. 2018, 8(1):15099, 12 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Joos et al., "Covalent attachment of hybridizable oligonucleotides to glass supports," Anal Biochem., Apr. 1997, 247(1):96-101.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Koch et al., "Photochemical immobilization of anthraquinone conjugated oligonucleotides and PCR amplicons on solid surfaces," Bioconjugate Chem., Jul. 2000, 11(4):474-483.
Korbel et al., "Paired-end mapping reveals extensive structural variation in the human genome," Science, 2007, 318(5849):420-426.
Korlach et al., "Selective aluminum passivation for targeted immobilization of single DNA polymerase molecules in zero-mode waveguide nanostructures," Proc. Natl. Acad. Sci. USA 105, 1176-1181, 2008.
Kozlov et al., "A highly scalable peptide-based assay system for proteomics," PLoS ONE, 2012, 7(6):e37441, 10 pages.
Kretschy et al., "Next-Generation o-Nitrobenzyl Photolabile Groups for Light-Directed Chemistry and Microarray Synthesis," Angewandte Chemie International Edition, Jul. 2015, 54(29):8555-8559.
Kristensen et al., "High-Throughput Methods for Detection of Genetic Variation," BioTechniques, Feb. 2001, 30(2):318-332.
Kurz et al., "cDNA-protein fusions: covalent protein-gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Autoantigen discovery with a synthetic human peptidome," Nature Biotechnology, May 2011, 29(6):535-541.
Lee et al., "Fluorescent in situ sequencing (FISSEQ) of RNA for gene expression profiling in intact cells and tissues," Nature Protocols, 2015, 10(3):442-458.

(56) References Cited

OTHER PUBLICATIONS

Leriche et al., "Cleavable linkers in chemical biology," Bioorganic & Medicinal Chemistry, 2012, 20:571-582.

Lietard et al., "High-Density RNA Microarrays Synthesized In Situ by Photolithography," Angew. Chem. Int. Ed. Engl., Nov. 2018, 57(46):15257-15261.

Linnarsson, "Recent advances in DNA sequencing methods—general principles of sample preparation," Experimental Cell Research, 2010, 316(8):1339-1343.

Liu et al., "An integrated and sensitive detection platform for biosensing application based on Fe@ Au magnetic nanoparticles as bead array carries," Biosens Bioelectron, Dec. 2010, 26(4):1442-8.

Liu et al., "High-Spatial-Resolution Multi-Omics Atlas Sequencing of Mouse Embryos via Deterministic Barcoding in Tissue," BioRxiv, 2019, 55 pages.

Liu et al., "Surface and interface control on photochemically initiated immobilization," J Am Chem Soc., Nov. 2006, 128(43):14067-72.

Lizardi et al., "Mutation detection and single-molecule counting using isothermal rolling-circle amplification," Nat. Genet., 1998, 19(3):225-232.

Lundberg et al., "Multiplexed homogeneous proximity ligation assays for high-throughput protein biomarker research in serological material," Mol Cell Proteomics, 2011, 10(4):M110.004978, 11 pages.

Marx, "Method of the Year: spatially resolved transcriptomics," Nature Methods, 2021, 18(1):9-14.

Mcgee, "Structure and Analysis of Affymetrix Arrays," UTSW Microarray Analysis Course, Oct. 28, 2005, 68 pages.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

Miller et al., "Basic concepts of microarrays and potential applications in clinical microbiology," Clinical Microbiology Reviews, 2009, 22(4):611-633.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Mitsuhashi et al., "Gene manipulation on plastic plates," Nature 357: 519-520, 1992.

Mizusawa et al., "A bacteriophage lambda vector for cloning with BamHI and Sau3A," Gene, 1982, 20(3):317-322.

Nikiforov et al., "The use of 96-well polystyrene plates for DNA hybridization-based assays: an evaluation of different approaches to oligonucleotide immobilization," Anal Biochem, May 1995, 227(1):201-9.

Nowak et al., "Entering the Postgenome Era," Science, 1995, 270(5235):368-71.

Oleinikov et al., "Self-assembling protein arrays using electronic semiconductor microchips and in vitro translation," J Proteome Res, May-Jun. 2003, 2(3): 313-319.

Pemov et al., "DNA analysis with multiplex microarray-enhanced PCR," Nucl. Acids Res., Jan. 2005, 33(2):e11, 9 pages.

Perler et al., "Intervening sequences in an Archaea DNA polymerase gen," Proc Natl Acad Sci USA, Jun. 1992, 89(12):5577-5581.

Petterson et al., "Generations of sequencing technologies," Genomics, 2009, 93(2):105-111.

Polsky-Cynkin et al., "Use of DNA immobilized on plastic and agarose supports to detect DNA by sandwich hybridization," Clin. Chem., 1985, 31(9):1438-1443.

Ramachandran et al., "Next-generation high-density self-assembling functional protein arrays," Nature Methods, Jun. 2008, 5(6):535-538.

Ranki et al., "Sandwich hybridization as a convenient method for the detection of nucleic acids in crude samples," Gene, 1983, 21(1-2):77-85.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Rodriques et al., "Slide-seq: A scalable technology for measuring genome-wide expression at high spatial resolution," Science, 2019, 363(6434):1463-1467.

Rogers et al., "Immobilization of oligonucleotides onto a glass support via disulfide bonds: A method for preparation of DNA microarrays," Anal Biochem., Jan. 1999, 266(1):23-30.

Ronaghi et al., "A sequencing method based on real-time pyrophosphate," Science, Jul. 1998, 281(5375):363-365.

Ronaghi et al., "Real-time DNA sequencing using detection of pyrophosphate release," Analytical Biochemistry, Nov. 1996, 242(1):84-89.

Ronaghi, "Pyrosequencing sheds light on DNA sequencing," Genome Res, Jan. 2001, 11(1):3-11.

Rouillard et al., "OligoArray 2.0: design of oligonucleotide probes for DNA microarrays using a thermodynamic approach," Nuc. Acid Research, Jun. 2003, 31(12): 3057-3062.

Rubina et al., "Hydrogel-based protein microchips: manufacturing, properties, and applications," Biotechniques, May 2003, 34(5):1008-14.

Running et al., "A procedure for productive coupling of synthetic oligonucleotides to polystyrene microtiter wells for hybridization capture," Biotechniques, Mar. 1990, 8(3):276-279.

Sack et al., "Express photolithographic DNA microarray synthesis with optimized chemistry and high-efficiency photolabile groups," Journal of Nanobiotechnology, Mar. 2016, 14:14, 13 pages.

Salmén et al., "Barcoded solid-phase RNA capture for Spatial Transcriptomics profiling in mammalian tissue sections," Nature Protocols, Oct. 2018, 13(11):2501-2534.

Saxonov et al., "10x Genomics, Mastering Biology to Advance Human Health," PowerPoint, 10x, 2020, 41 pages.

Schena et al., "Quantitative monitoring of gene expression patterns with a complementary DNA microarray," Science, Oct. 1995, 270(5235):467-470.

Schlapak et al., "Glass surfaces grafted with high-density poly (ethylene glycol) as substrates for DNA oligonucleotide microarrays," Langinuir, Jan. 2006, 22: 277-285.

Schwartz et al., "Capturing native long-range contiguity by in situ library construction and optical sequencing." PNAS, Nov. 13, 2012, 109(46):18749-18754.

Seurynck-Servoss et al., "Evaluation of Surface Chemistries for Antibody Microarrays," Anal Biochem., 371(1):105-115, 2007.

Shalon et al., "A DNA microarray system for analyzing complex DNA samples using two-color fluorescent probe hybridization," Genome Res., Jul. 1996, 6(7):639-45.

Stahl et al., "Visualization and analysis of gene expression in tissue sections by spatial transcriptomics," Science, Jun. 2016, 353(6294):78-82.

Stahl et al., "Visualization and analysis of gene expression in tissue sections by spatial transcriptomics," Supplementary Materials, Science, Jul. 2016, 353(6294):78-82, 41 pages.

Stimpson et al., "Real-time detection of DNA hybridization and melting on oligonucleotide arrays by using optical wave guides," Proc Natl Acad Sci USA, Jul. 1995, 92(14):6379-83.

Strell et al., "Placing RNA in context and space—methods for spatially resolved transcriptomics," The FEBS Journal, 2019, 286(8):1468-1481.

Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.

Timofeev et al., "Regioselective immobilization of short oligonucleotides to acrylic copolymer gels," Nucleic Acids Res., Aug. 1996, 24(16):3142-8.

Trejo et al., "Extraction-free whole transcriptome gene expression analysis of FFPE sections and histology-directed subareas of tissue," PLoS ONE, Feb. 2019, 14(2):e0212031, 22 pages.

Twyman et al.. "Techniques Patents for SNP Genotyping," Pharmacogenomics, Jan. 2003, 4(1):67-79.

(56) References Cited

OTHER PUBLICATIONS

Van Gelder et al., "Amplified RNA synthesized from limited quantities of heterogeneous cDNA," Proc. Natl. Acad. Sci. USA, 1990, 87(5):1663-1667.
Van Ness et al., "A versatile solid support system for oligodeoxynucleotide probe-based hybridization assays", Nucleic Acids Res., 19:3345-3350, 1991.
Vasiliskov et al., "Fabrication of microarray of gel-immobilized compounds on a chip by copolymerization," Biotechniques, Sep. 1999, 27(3):592-606.
Vickovic et al., "High-definition spatial transcriptomics for in situ tissue profiling," Nat Methods, Oct. 2019, 16(10):987-990.
Vogelstein et al., "Digital PCR," Proceedings of the National Academy of Sciences, Aug. 1999, 96(16):9236-9241.
Walker et al., "Strand displacement amplification—an isothermal, in vitro DNA amplification technique," Nucleic Acids Research, 1992, 20(7):1691-1696.
Wang et al., "Imaging-based pooled CRISPR screening reveals regulators of lncRNA localization," Proc Natl Acad Sci USA, May 2019, 116(22):10842-10851.
Wang et al., "High-fidelity mRNA amplification for gene profiling," Nature Biotechnology, Apr. 2000, 18(4):457-459.
Worthington et al., "Cloning of random oligonucleotides to create single-insert plasmid libraries," Anal Biochem, 2001, 294(2):169-175.
Yershov et al., "DNA analysis and diagnostics on oligonucleotide microchips," Proc. Natl. Acad. Sci. USA, May 1996, 93(10):4913-4918.
Zhu et al., "Reverse transcriptase template switching: a SMART approach for full-length cDNA library construction," Biotechniques, Apr. 2001, 30(4):892-897.
U.S. Appl. No. 63/033,348, filed Jun. 2, 2020, Bent.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Codeluppi et al., "Spatial organization of the somatosensory cortex revealed by osmFISH," Nature Methods, Nov. 2018, 15:932-935.
Eng et al., "Transcriptome-scale super-resolved imaging in tissues by RNA seqFISH+," Nature, Apr. 2019, 568(7751):235-239, 37 pages.
Goh et al., "Highly Specific Multiplexed RNA Imaging in Tissues With Split-FISH," Nat Methods, Jun. 15, 2020, 17(7):689-693, 21 pages.
Liu et al., "High-Spatial-Resolution Multi-Omnics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Takei et al., "Integrated Spatial Genomics Reveals Global Architecture of Single Nuclei," Nature, Jan. 27, 2021, 590(7845):344-350, 53 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Asp et al., "Spatially Resolved Transcriptomes—Next Generation Tools for Tissue Exploration," Bioessays, Oct. 2020, 42(10):e1900221, 16 pages.
Bergenstråhle et al., "Seamless integration of image and molecular analysis for spatial transcriptomics workflows," BMC Genomics, Jul. 2020, 21(1):482, 7 pages.
Bolotin et al., "MiXCR: software for comprehensive adaptive immunity profiling," Nat Methods., May 2015, 12(5):380-1.
Burgess, "Spatial transcriptomics coming of age," Nat Rev Genet., Jun. 2019, 20(6):317, 1 page.
U.S. Appl. No. 16/353,937, filed Mar. 14, 2019, Frisen et al.
U.S. Appl. No. 17/707,189, filed Mar. 29, 2022, Chell et al.
Dalma-Weiszhausz et al., "The affymetrix GeneChip platform: an overview," Methods Enzymol., 2006. 410:3-28.
Escholarship.org [online], "Methods and devices for fabricating and assembling DNA and protein arrays for high-throughput analyses [electronic resource]," 2010, retrieved on Jun. 8, 2022, retrieved from URL<https://escholarship.org/uc/item/6tf7p46s>, 155 pages.
Jennane et al., "Photolithography of self-assembled monolayers: optimization of protecting groups by an electroanalytical method," Can. J Chem., Dec. 1996, 74(12):2509-2517.
Miller et al., "Chapter 11—Solid and Suspension Microarrays for Microbial Diagnostics," Methods in Microbiology, 2015, 42:395-431.
Vickovic et al., "SM-Omics: An automated Platform for High-Throughput Spatial Multi-Omics," bioRxiv, Oct. 2020, 40 pages.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

\* cited by examiner

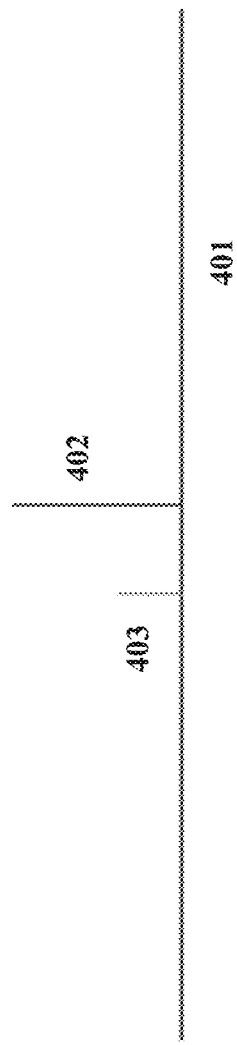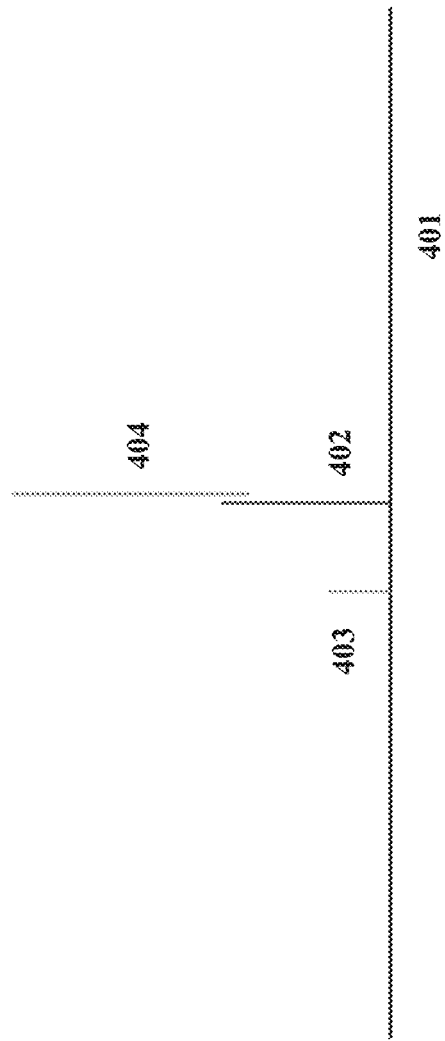
FIG. 4A
FIG. 4B

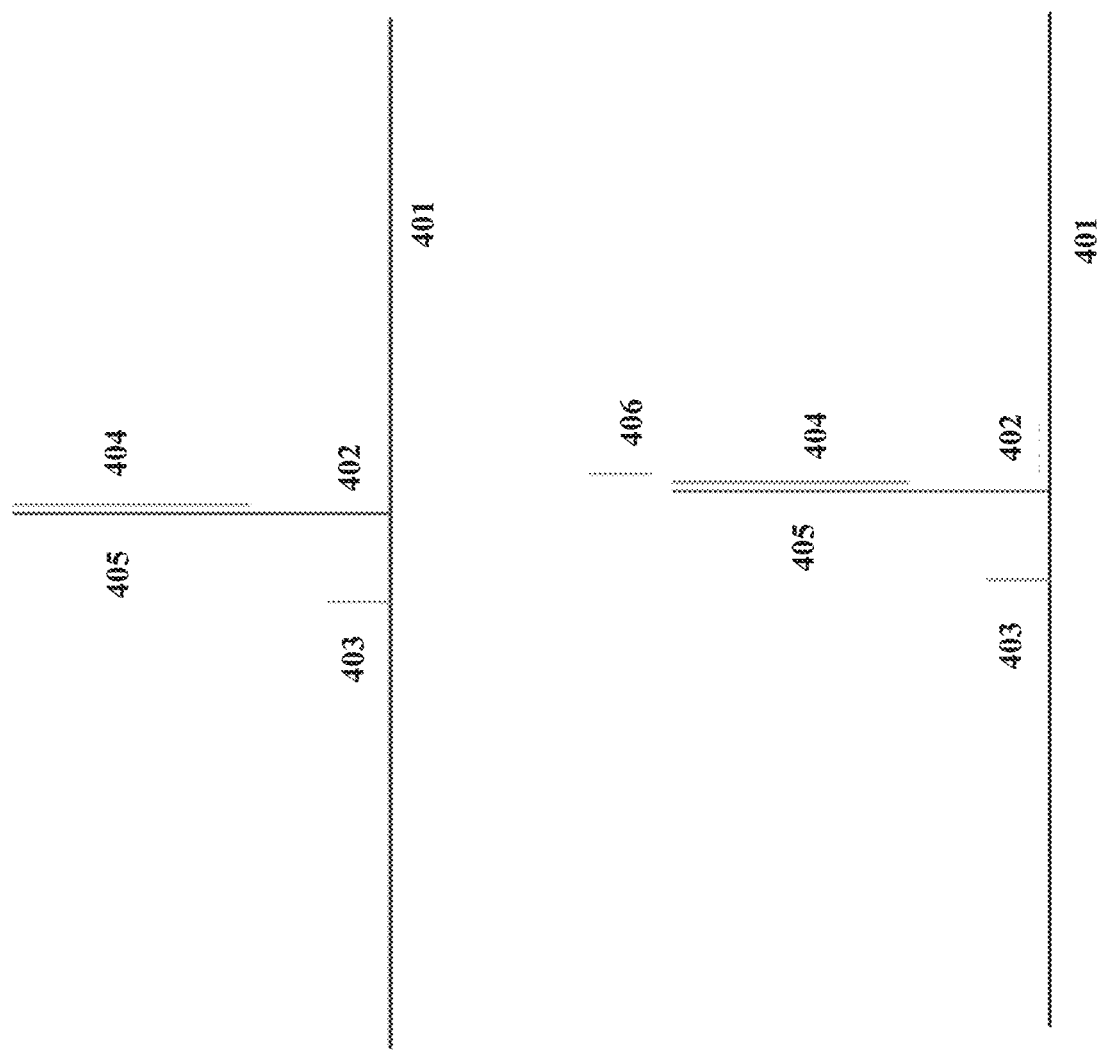

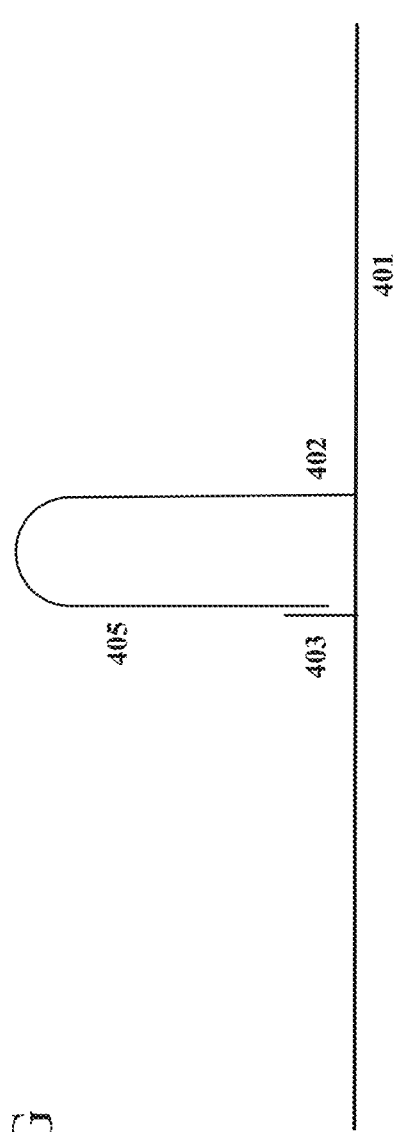
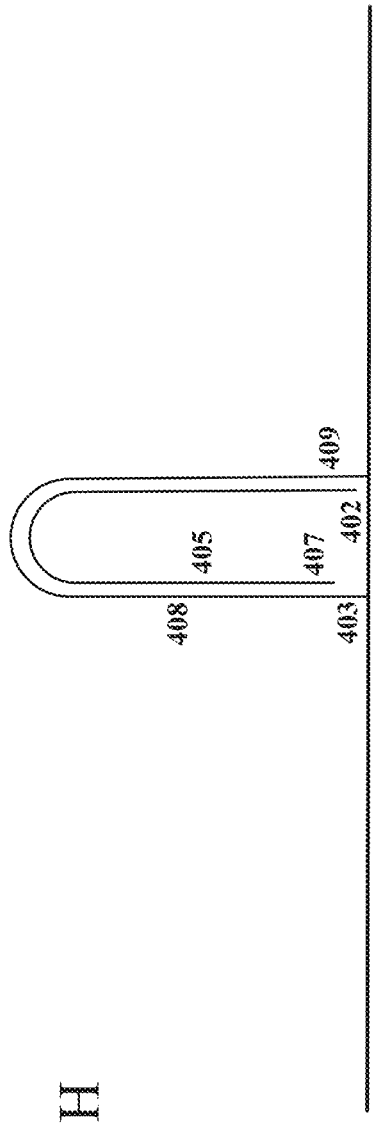
FIG 4G
FIG 4H

COMPOSITIONS AND METHODS OF MAKING GENE EXPRESSION LIBRARIES

CROSS-REFERENCE TO RELATED APPLICATIONS

This application claims priority to U.S. Provisional Patent Application No. 62/967,361, filed Jan. 29, 2020 and U.S. Provisional Patent Application No. 63/033,566, filed Jun. 2, 2020; each of which is incorporated herein by reference in its entirety.

SEQUENCE LISTING

This application contains a Sequence Listing that has been submitted electronically as an ASCII text file named "47706-0154001 SL ST25.txt." The ASCII text file, created on Aug. 17, 2023, is 2,082 bytes in size. The material in the ASCII text file is hereby incorporated by reference in its entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

SUMMARY

This application is based on the discoveries of a method of making a spatial 5' gene expression library and arrays for use in methods that allow for spatial analysis of large target analytes, e.g., V(D)J (or VDJ) rearranged T-cell receptors or immunoglobulins, a method for detecting and/or analyzing the 5' sequence of a polynucleotide of interest, and a method for removing sequences from a polynucleotide of interest to facilitate detection and/or analysis of a 5' sequence of the polynucleotide.

In one aspect, methods are provided for determining a location of a target nucleic acid in a biological sample that include: (a) contacting the biological sample with an array comprising a feature, wherein the feature comprises an attached first and second probe, wherein: a 5' end of the first probe is attached to the feature; the first probe comprises in a 5' to a 3' direction: a spatial barcode and a capture domain (e.g., a poly(T) capture domain), wherein the poly(T) capture domain binds specifically to the target nucleic acid; a 5' end of the second probe is attached to the feature; a 3' end of the second probe is reversibly blocked; and the second probe comprises a poly(GI) capture domain; (b) extending a 3' end of the first probe to add a sequence that is complementary to a portion of the target nucleic acid; (c) ligating an adapter to the 5' end of the target nucleic acid specifically bound to the first probe; (d) adding a sequence complementary to the adapter to the 3' end of the first probe; (e) adding non-templated cytosines to the 3' end of the first probe to generate a poly(C) sequence, wherein the poly(C) sequence specifically binds to the poly(GI) capture domain of the second probe; (f) unblocking the 3' end of the second probe and extending the 3' end of the second probe to add a sequence comprising a sequence in the target nucleic acid and a sequence that is complementary to the spatial barcode; (g) cleaving a region of the second probe at a cleavage site that is 5' to the poly(GI) capture domain, thereby releasing the second probe from the feature; and (h) determining (i) all or a part of the sequence of the spatial barcode, or a complement thereof, and (ii) all or a part of the sequence of the target nucleic acid, or a complement thereof, and using the sequences of (i) and (ii) to determine the location of the target nucleic acid in the biological sample.

In some embodiments of any of the methods described herein, the poly(GI) capture domain comprises a sequence of $(GGI)_n$, wherein n is about 3 to about 20.

In some embodiments of any of the methods described herein, step (h) comprises sequencing all or a part of the sequence of the spatial barcode, or a complement thereof, and sequencing all of a part of the sequence of the target nucleic acid, or a complement thereof. In some embodiments of any of the methods described herein, the sequencing is performed using high throughput sequencing.

In some embodiments of any of the methods described herein, the first probe further comprises a unique molecular identifier (UMI), wherein the UMI in the first probe is positioned 5' to the poly(T) capture domain in the first probe.

In some embodiments of any of the methods described herein, the second probe further comprises a unique molecule identifier (UMI), wherein the UMI in the second probe is positioned 5' to the poly(GI) capture sequence in the second probe, wherein the UMI in the second probe is 3' positioned relative to the cleavage site in the second probe.

In some embodiments of any of the methods described herein, the UMI in the first probe and the UMI in the second probe comprise different sequences. In some embodiments of any of the methods described herein, the UMI in the first probe and the UMI in the second probe comprise the same sequence.

In some embodiments of any of the methods described herein, the second probe further comprises an spatial barcode, wherein the spatial barcode in the second probe is 3' positioned relative to the cleavage site in the second probe.

In some embodiments of any of the methods described herein, the spatial barcode in the first probe and the spatial barcode in the second probe comprise different sequences. In some embodiments of any of the methods described herein, the spatial barcode in the first probe and the spatial barcode in the second probe comprise the same sequence.

In some embodiments of any of the methods described herein, the target nucleic acid is RNA. In some embodiments of any of the methods described herein, the RNA is an mRNA. In some embodiments of any of the methods described herein, mRNA encodes a T-cell receptor.

Some embodiments of any of the methods described herein further include determining a sequence encoding one or more complementarity determining region(s) (CDR(s)) of the T-cell receptor.

In some embodiments of any of the methods described herein, the mRNA encodes an immunoglobulin heavy or light chain. In some embodiments of any of the methods described herein, the method further comprises determining a sequence encoding one or more CDR(s) of the immunoglobulin heavy or light chain.

In some embodiments of any of the methods described herein, the array is a bead array. In some embodiments of any of the methods described herein, the array is a slide.

In some embodiments of any of the methods described herein, the biological sample is a tissue section. In some embodiments of any of the methods described herein, the tissue section is a formalin-fixed and paraffin-embedded (FFPE) tissue section. In some embodiments of any of the methods described herein, the tissue section is a fresh frozen tissue section.

Also provided herein are arrays comprising a feature, where the feature comprises an attached first and second probe, wherein: a 5' end of the first probe is attached to the feature; the first probe comprises in a 5' to a 3' direction: a spatial barcode and a poly(T) capture domain, where the poly(T) capture domain binds specifically to the target nucleic acid; a 5' end of the second probe is attached to the feature; a 3' end of the second probe is reversibly blocked; and the second probe comprises a poly(GI) capture domain. In some embodiments of any of the arrays described herein, the poly(GI) capture domain comprises a sequence of (GGI)n, wherein n is about 3 to about 20.

In some embodiments of any of the arrays described herein, the first probe further comprises a unique molecular identifier (UMI), wherein the UMI in the first probe is positioned 5' to the poly(T) capture domain in the first probe.

In some embodiments of any of the arrays described herein, the second probe further comprises a unique molecule identifier (UMI), wherein the UMI in the second probe is positioned 5' to the poly(GI) capture sequence in the second probe, wherein the UMI in the second probe is 3' positioned relative to the cleavage site in the second probe.

In some embodiments of any of the arrays described herein, the UMI in the first probe and the UMI in the second probe comprise different sequences. In some embodiments of any of the arrays described herein, the UMI in the first probe and the UMI in the second probe comprise the same sequence.

In some embodiments of any of the arrays described herein, the second probe further comprises a spatial barcode, wherein the spatial barcode in the second probe is 3' positioned relative to the cleavage site in the second probe.

In some embodiments of any of the arrays described herein, the spatial barcode in the first probe and the spatial barcode in the second probe comprise different sequences. In some embodiments of any of the arrays described herein, the spatial barcode in the first probe and the spatial barcode in the second probe comprise the same sequence.

In some embodiments of any of the arrays described herein, the array is a bead array. In some embodiments of any of the arrays described herein, the array is a slide.

In another aspect, a method is provided for detecting and/or determining a location of a biological analyte within a biological sample. The method comprises: (a) contacting a biological sample with a substrate, wherein the substrate comprises an attached first and second probe, wherein: a 5' end of the first probe is attached to the substrate; the first probe comprises, in a 5' to 3' direction: a spatial barcode and a first capture domain; a 5' end of the second probe is attached to the substrate; and the second probe comprises a second capture domain, wherein a target polynucleotide sequence of a biological analyte within the biological sample binds to the first capture domain; (b) extending a 3' end of the first probe to generate an extension product that comprises a nucleotide sequence that is complementary to the target polynucleotide sequence, or a portion thereof (c) attaching an adapter to the 3' end of the extension product, wherein the adapter comprises a sequence that is complementary to the sequence of the second capture domain; (d) hybridizing the adapter to the second capture domain; and (e) extending a 3' end of the second capture domain, thereby generating a nucleotide sequence that comprises a 5' sequence of the target polynucleotide sequence of the biological analyte proximal to the sequence of the second capture domain.

In some embodiments, attaching the adaptor in step (c) comprises adding untemplated nucleotides to the 3' end of the extension product, hybridizing a template switching oligonucleotide to the untemplated nucleotides, and extending the 3' end of the extension product, thereby generating the adapter, wherein the adapter comprises a sequence that is complementary to the sequence of the template switching oligonucleotide. The untemplated nucleotides may include any nucleotides or nucleotide sequences thereof. In some embodiments, the untemplated nucleotides comprise a poly (C) or a poly(G) sequence.

In some embodiments, attaching the adaptor in step (c) includes ligating the adapter to the 3' end of the extension product.

In some embodiments, step (b) and/or (e) comprises extending the 3' end of the first probe or the second probe, respectively, with a reverse transcriptase or polymerase (e.g., RNA polymerase or DNA polymerase).

In some embodiments, step (a) further comprises permeabilizing the biological sample prior to or after contacting the substrate.

In various embodiments, the biological sample may be a tissue section, a primary cell, a cell line, or an organoid. For example, the biological sample may be a formalin-fixed and paraffin-embedded (FFPE) or paraformaldehyde (PFA) tissue section or a fresh frozen tissue section.

The target polynucleotide may comprise DNA, RNA. The first capture domain may comprise a poly(dT) sequence, a random sequence, or a sequence that is complementary to a target sequence of interest. In one embodiment, the target polynucleotide comprises mRNA. For example, the mRNA may encode a T-cell receptor or B-cell receptor, and in one embodiment, the method further comprises determining a sequence that encodes one or more complementarity determining region(s) (CDR(s)) of the T-cell receptor or B-cell receptor. For example, the mRNA may encode an immunoglobulin heavy or light chain, and in one embodiment, the method further comprises determining a sequence that encodes one or more CDR(s) of the immunoglobulin heavy or light chain.

In some embodiments, at least one of the first probe and the second probe further comprises a unique molecular identifier (UMI) positioned 5' to the respective capture domain. In one embodiment, the first and second probes each comprise a UMI, and the UMI in the first probe and the UMI in the second probe comprise different sequences.

In some embodiments, the second probe further comprises a spatial barcode positioned 5' to the second capture domain. In one embodiment, the spatial barcode in the first probe and the spatial barcode in the second probe comprise different sequences. In another embodiment, the spatial barcode in the first probe and the spatial barcode in the second probe comprise the same sequence.

In some embodiments, the substrate comprises an array comprising a feature, wherein the first and second polynucleotide probes are attached to the feature. For example, the array may be a bead array (for example, gel beads) or a slide.

In some embodiments, a plurality of first and second probes are attached to the substrate, and the ratio of first probes to second probes on the substrate is about 1:1000 to about 1000:1, or about 1:1 to about 1:100.

In some embodiment, the first and second probes are directly attached to the substrate. In other embodiments, the first and second probes are indirectly attached to the substrate. For example, the first and second probes may be attached to beads and the beads attached to the substrate.

The method may further comprise: (f) determining (i) all or a portion of the target polynucleotide sequence or a complement thereof, and (ii) the sequence of all or a portion of the spatial barcode, or a complement thereof, and using the determined sequences of (i) and (ii) to identify the location of the biological analyte in the biological sample. Prior to step (f), the method may comprise: generating an amplification product from the extension product generated in step (e), wherein the amplification product comprises the 5' sequence of the target polynucleotide or the complement thereof, and wherein step (f) comprises determining the sequences of (i) and (ii) using the amplification product. Prior to step (f), the method may comprise: cleaving a region of the second probe at a cleavage site that is 5' to the second capture domain, thereby releasing the second probe from the substrate.

In another aspect, a method is provided for detecting a biological analyte within a biological sample. The method comprises: (a) hybridizing first and second oligonucleotides to a template polynucleotide, wherein the template polynucleotide comprises a polynucleotide sequence of a biological analyte or a complement thereof; wherein: the first oligonucleotide comprises a sequence that is complementary to a first sequence of the template polynucleotide; the second oligonucleotide is a bridging oligonucleotide that comprises: sequences that are complementary to second and third sequences of the template polynucleotide, and a 5' phosphate group, wherein the second and third sequences of the template polynucleotide are 3' and 5', respectively, to a fourth sequence that comprises a polynucleotide region to be removed from the template polynucleotide; wherein the first sequence of the template polynucleotide is 3' to the second sequence of the template polynucleotide; (b) extending 3' ends of the first and second oligonucleotides, thereby producing extended first and second oligonucleotides, wherein extension of the first oligonucleotide ceases when the 5' phosphate of the second oligonucleotide is reached, thereby resulting in a nick between the extended first and second oligonucleotides; and (c) ligating the 3' end of the extended first oligonucleotide and the 5' phosphate of the extended second oligonucleotide, thereby producing a polynucleotide product that comprises a complement of 5' and 3' portions of the template polynucleotide sequence and does not comprise the complement of the fourth sequence of the template polynucleotide.

In some embodiments, the first sequence of the template polynucleotide to which the first oligonucleotide hybridizes is at the 3' end of the template polynucleotide.

In some embodiments, the first sequence of the template polynucleotide to which the first oligonucleotide hybridizes is an adapter that is attached to the 3' end of the template polynucleotide. In one embodiment, prior to step (a): (i) untemplated nucleotides are added to the 3' end of the template polynucleotide; a template switching oligonucleotide is hybridized to the untemplated nucleotides; and (ii) the 3' end of the template polynucleotide is extended, thereby generating the adapter, wherein the adapter is complementary to the sequence of the template switching oligonucleotide. The untemplated nucleotides may comprise any nucleotides or sequence of nucleotides. In some embodiments, the untemplated nucleotides comprise a poly (C) or poly(G) sequence. In another embodiment, prior to step (a), the adapter is ligated to the 3' end of the template polynucleotide.

In some embodiments, step (b) comprises extending the 3' ends of the first and second oligonucleotides with a non-strand displacing, non 5'-3' exonuclease DNA polymerase.

In some embodiments, step (c) comprises ligation with a DNA ligase.

In some embodiments, the template polynucleotide comprises a barcode sequence and/or a UMI.

In some embodiments, the first and second oligonucleotides are about 10 to about 50 nucleotides in length. In some embodiments, the second and third sequences of the extension product to which the second oligonucleotide hybridizes are about 10 to about 50 nucleotides in length. In some embodiments, the second oligonucleotide comprises a linker between the sequences that are complementary to the second and third sequences of the extension product. The linker may be any nucleotide sequence, e.g., a sequence that is not complementary to a sequence of the extension product. In one embodiment, the linker comprises the sequence (AT)n. In some embodiments, the linker is about 1 to about 50 nucleotides in length.

In some embodiments, the method further comprises: (d) determining all or a portion of the 5' and 3' portions of the template polynucleotide sequence (the sequences that are 5' and 3' to the fourth sequence of the template polynucleotide) or a complement thereof. Prior to step (d), the method may comprise: generating an amplification product from the polynucleotide product generated in step (c).

In another aspect, a method is provided for detecting a biological analyte within a biological sample, said method comprising: (a) contacting a biological sample with a probe, wherein: the probe comprises, in a 5' to 3' direction: a barcode and a capture domain, wherein a template polynucleotide sequence of a biological analyte within the biological sample hybridizes to the capture domain; (b) extending a 3' end of the probe to generate an extension product that comprises a nucleotide sequence that is complementary to the template polynucleotide sequence, or a portion thereof; (c) hybridizing first and second oligonucleotides to the extension product, wherein: the first oligonucleotide comprises: a sequence that is complementary to a first sequence of the extension product; the second oligonucleotide is a bridging oligonucleotide that comprises: sequences that are complementary to second and third sequences that are flanking a polynucleotide region to be removed from the extension product, and a 5' phosphate group, wherein the second and third sequences of the extension product are 3' and 5', respectively, to a fourth sequence that comprises the polynucleotide region to be removed from the extension product, and wherein the second, third, and fourth sequences of the extension product are complementary to sequences of the template polynucleotide sequence, and wherein the first sequence of the extension product is 3' to the second sequence of the extension product; (d) extending 3' ends of the first and second oligonucleotides, thereby producing extended first and second oligonucleotides, wherein extension of the first oligonucleotide ceases when the 5' phosphate of the second oligonucleotide is reached, thereby resulting in a nick between the extended first and second oligonucleotides; and (e) ligating the 3' end of the extended first oligonucleotide and the 5' phosphate of the extended second oligonucleotide, thereby producing a polynucleotide product that comprises a complement of 5' and 3' portions of the extension product, wherein the polynucleotide product and does not comprise the complement of the fourth sequence of the extension product.

In some embodiments, the probe further comprises a UMI positioned 5' to the capture domain.

In some embodiments, the first sequence of the extension product to which the first oligonucleotide hybridizes is at the 3' end of the template polynucleotide.

In some embodiments, the first sequence of the extension product to which the first oligonucleotide hybridizes is an adapter that is attached to the 3' end of the extension product. In one embodiment, prior to step (a): (i) untemplated nucleotides are added to the 3' end of the extension product; a template switching oligonucleotide is hybridized to the untemplated nucleotides; and (ii) the 3' end of the extension product is extended, thereby generating the adapter sequence, wherein the adapter sequence is complementary to the sequence of the template switching oligonucleotide. The untemplated nucleotides may comprise any nucleotides or sequence of nucleotides. In some embodiments, the untemplated nucleotides comprise a poly(C) or poly(G) sequence. In another embodiment, prior to step (a), the adapter is ligated to the 3' end of the extension product.

In some embodiments, step (b) comprises extending the 3' end of the probe with a RNA dependent or DNA dependent DNA polymerase.

In some embodiments, step (d) comprises extending the 3' ends of the first and second oligonucleotides with a non-strand displacing, non 5'-3' exonuclease DNA polymerase.

In some embodiments, step (e) comprises ligation with a DNA ligase.

In some embodiments, step (b) comprises incorporation of uridine residues into the extension product, and the method further comprises: (f) digesting the extension product with a uracil specific excision reagent.

In some embodiments, the first and second oligonucleotides are about 10 to about 50 nucleotides in length. In some embodiments, the second and third sequences of the extension product to which the second oligonucleotide hybridizes are about 10 to about 50 nucleotides in length. In some embodiments, the second oligonucleotide comprises a linker between the sequences that are complementary to the second and third sequences of the extension product. The linker may be any nucleotide sequence, e.g., a sequence that is not complementary to a sequence of the extension product. In one embodiment, the linker comprises the sequence (AT)n. In some embodiments, the linker is about 1 to about 50 nucleotides in length.

In some embodiments, the polynucleotide probe comprises a barcode sequence 5' to the capture domain, for example, a cell barcode sequence or a spatial barcode sequence.

In some embodiments, wherein step (a) further comprises permeabilizing the biological sample prior to or after contacting the substrate.

In some embodiments, step (a) further comprises permeabilizing the biological sample prior to or after contacting the substrate.

In various embodiments, the biological sample may be a tissue section, a primary cell, a cell line, or an organoid. For example, the biological sample may be a formalin-fixed and paraffin-embedded (FFPE) tissue section or a fresh frozen tissue section.

The target polynucleotide may comprise DNA, RNA. The first capture domain may comprise a poly(dT) sequence, a random sequence, or a sequence that is complementary to a template polynucleotide sequence of interest. In one embodiment, the target polynucleotide comprises mRNA. For example, the mRNA may encode a T-cell receptor or B-cell receptor, and in one embodiment, the method further comprises determining a sequence that encodes one or more complementarity determining region(s) (CDR(s)) of the T-cell receptor or B-cell receptor. For example, the mRNA may encode an immunoglobulin heavy or light chain, and in one embodiment, the method further comprises determining a sequence that encodes one or more CDR(s) of the immunoglobulin heavy or light chain.

In some embodiments, the 5' end of the probe is attached to the substrate. In some embodiments, the substrate comprises an array comprising a feature, wherein the 5' end of the probe is attached to the feature. For example, the array may be a bead array (for example, gel beads) or a slide.

In some embodiment, the probe is directly attached to the substrate. In other embodiments, the probe is indirectly attached to the substrate. For example, the probe may be attached to beads and the beads attached to the substrate.

In some embodiments, the method further comprises: (f) determining (i) all or a portion of the 5' and 3' portions of the template polynucleotide sequence, or a complement thereof, and (ii) the sequence of all or a portion of a spatial barcode sequence, or a complement thereof, and using the determined sequences of (i) and (ii) to identify the location of the biological analyte in the biological sample. Prior to step (f), the method may further comprise: generating an amplification product from the polynucleotide product generated in step (e), and wherein step (f) comprises determining the sequences of (i) and (ii) using the amplification product.

In some embodiments, the present invention provides for kits that comprise arrays for practicing the methods described herein. The array of a kit can comprise a feature, where the feature comprises an attached first and second probe, wherein: a 5' end of the first probe is attached to the feature; the first probe comprises in a 5' to a 3' direction: a spatial barcode and a poly(T) capture domain, where the poly(T) capture domain binds specifically to the target nucleic acid; a 5' end of the second probe is attached to the feature; a 3' end of the second probe is reversibly blocked; and the second probe comprises a poly(GI) capture domain. A kit can comprise enzymes, buffers, reagents, etc. for practicing the methods disclosed here. Further, a kit can include instructions such that users of the kit would understand how to use the kit to capture a target analyte (e.g. a nucleic acid) from a biological sample and determine its location.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 4A-4J depict an exemplary workflow for detecting and/or determining spatial location of a target polynucleotide of interest.

DETAILED DESCRIPTION

Figure 1:
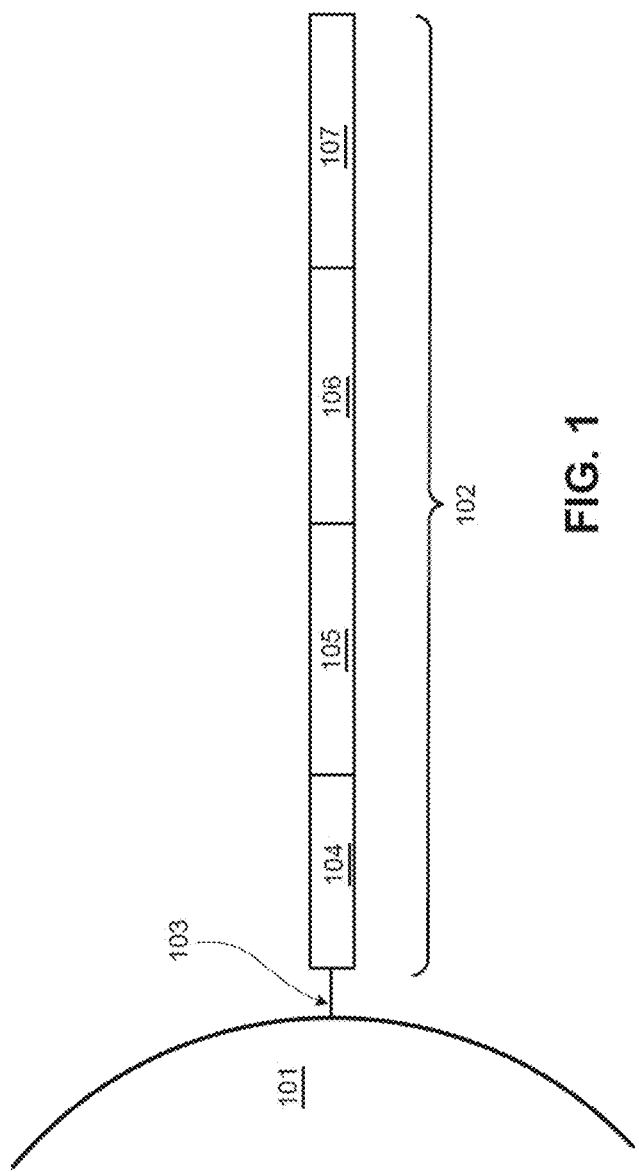
FIG. 1 is a schematic diagram showing an example of a barcoded capture probe, as described herein.

Provided herein are methods of determining a location of a target nucleic acid in a biological sample that include: (a) contacting the biological sample with an array comprising a feature, wherein the feature comprises an attached first and second probe, where: a 5' end of the first probe is attached to the feature; the first probe comprises in a 5' to a 3' direction: a spatial barcode and a poly(T) capture domain, where the poly(T) capture domain binds specifically to the target nucleic acid; a 5' end of the second probe is attached to the feature; a 3' end of the second probe is reversibly blocked; and the second probe comprises a poly(GI) capture domain; (b) extending a 3' end of the first probe to add a sequence that is complementary to a portion of the target nucleic acid; (c) ligating an adapter to the 5' end of the target nucleic acid specifically bound to the first probe; (d) adding a sequence complementary to the adapter to the 3' end of the first probe; (e) adding non-templated cytosines to the 3' end of the first probe to generate a poly(C) sequence, where the poly(C) sequence specifically binds to the poly(GI) capture domain of the second probe; (f) unblocking the 3' end of the second probe and extending the 3' end of the second probe to add a sequence comprising a sequence in the target nucleic acid and a sequence that is complementary to the spatial barcode; (g) cleaving a region of the second probe at a cleavage site that is 5' to the poly(GI) capture domain, thereby releasing the second probe from the feature; and (h) determining (i) all or a part of the sequence of the spatial barcode, or a complement thereof, and (ii) all or a part of the sequence of the target nucleic acid, or a complement thereof, and using the sequences of (i) and (ii) to determine the location of the target nucleic acid in the biological sample.

Also provided herein are arrays comprising a feature, where the feature comprises an attached first and second probe, wherein: a 5' end of the first probe is attached to the feature; the first probe comprises in a 5' to a 3' direction: a spatial barcode and a poly(T) capture domain, where the poly(T) capture domain binds specifically to the target nucleic acid; a 5' end of the second probe is attached to the feature; a 3' end of the second probe is reversibly blocked; and the second probe comprises a poly(GI) capture domain.

I. Introduction

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774, 374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/ 0277663, 2020/024641, 2019/330617, 2019/264268, 2020/ 256867, 2020/224244, 2019/194709, 2019/161796, 2019/ 085383, 2019/055594, 2018/216161, 2018/051322, 2018/ 0245142, 2017/241911, 2017/089811, 2017/067096, 2017/ 029875, 2017/0016053, 2016/108458, 2015/000854, 2013/ 171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. In some embodiments, a biological sample can be a blood sample, a tumor sample, a lymph node sample, or a thymus sample. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951, 864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

II. Spatial 5' Gene Expression of VDJ Libraries

Provided herein are methods of determining a location of a target nucleic acid in a biological sample that include: (a) contacting the biological sample with an array comprising a feature, where the feature comprises an attached first and second probe, wherein: a 5' end of the first probe is attached to the feature; the first probe comprises in a 5' to a 3' direction: a spatial barcode and a poly(T) capture domain, where the poly(T) capture domain binds specifically to the target nucleic acid; a 5' end of the second probe is attached to the feature; a 3' end of the second probe is reversibly blocked; and the second probe comprises a poly(GI) capture domain; (b) extending a 3' end of the first probe to add a sequence that is complementary to a portion of the target nucleic acid; (c) ligating an adapter to the 5' end of the target nucleic acid specifically bound to the first probe; (d) adding a sequence complementary to the adapter to the 3' end of the first probe; (e) adding non-templated cytosines to the 3' end of the first probe to generate a poly(C) sequence, where the poly(C) sequence specifically binds to the poly(GI) capture domain of the second probe; (f) unblocking the 3' end of the second probe and extending the 3' end of the second probe to add a sequence comprising a sequence in the target nucleic acid and a sequence that is complementary to the spatial barcode; (g) cleaving a region of the second probe at a cleavage site that is 5' to the poly(GI) capture domain, thereby releasing the second probe from the feature; and (h) determining (i) all or a part of the sequence of the spatial barcode, or a complement thereof, and (ii) all or a part of the sequence of the target nucleic acid, or a complement thereof, and using the sequences of (i) and (ii) to determine the location of the target nucleic acid in the biological sample. In some embodiments, a feature can include two or more pairs of a first and a second probe (e.g., any of the first and second probes described herein). A first pair of a first and a second probe at a feature, as compared to a second pair of a first and a second probe at the feature, can have a different first and/or second probe as compared to first and/or second probe of the second pair (e.g., a different capture domain in the first probe and/or a different barcode in the first and/or second probes). In some embodiments, the spatial barcode in the first probe of the first pair and the spatial barcode in the first probe of the second pair are the same. In some embodiments, the spatial barcode in the first probe of the first pair and the spatial barcode in the first probe of the second pair are different. In some embodiments, the capture domain of the first probe of the first pair is the same as the capture domain of the first probe of the second pair. In some embodiments, the capture domain of the first probe of the first pair is different from the capture domain of the first probe of the second pair.

In some embodiments, the capture domain on the first probe has a poly(T) capture domain, where the poly(T) capture domain is configured to interact with the target nucleic acid (e.g., positioned at the 3' end of the first probe). For example, the poly(T) capture domain specifically binds to a messenger RNA (mRNA), via the poly(A) tail of the mRNA. For example, a poly(T) capture domain can include at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30 contiguous thymidines.

In some embodiments, the poly(GI) capture domain of the second probe is configured to interact with a poly(C) tail of an oligonucleotide, e.g., a poly(C) tail added to the 3' end of the extended first probe. In some embodiments, the poly(C) tail is added to the 3' end of the first probe after the extension of the first probe to add a sequence that is complementary to a portion of the target nucleic acid. In some embodiments, the poly(GI) capture domain comprises a sequence of at least 5 contiguous guanosine(s) and/or inosine(s). For example, a poly(GI) capture domain comprises a sequence of (GGI)n, wherein n is about 3 to about 20. In some embodiments, the poly(GI) capture domain comprises a sequence of (GGI)n, wherein n is 1, 2, 3, 4, 5, 6, 7, 8, 9, 10, 11, 12, 13, 14, 15, 16, 17, 18, 19, or 20. For example, a poly(GI) capture domain comprises a sequence of (GI)n, wherein n is about 4 to about 30. For example, a poly(GI) capture domain comprises a sequence of (GI)n, wherein n is 4, 5, 6, 7, 8, 9, 10, 11, 12, 13, 14, 15, 16, 17, 18, 19, 20, 21, 22, 23, 24, 25, 26, 27, 28, 29, or 30. For example, a poly(GI) capture domain comprises a sequence of (IG)n, wherein n is about 4 to about 30. For example, a poly(GI) capture domain comprises a sequence of (IG)n, wherein n is 4, 5, 6, 7, 8, 9, 10, 11, 12, 13, 14, 15, 16, 17, 18, 19, 20, 21, 22, 23, 24, 25, 26, 27, 28, 29, or 30.

In some embodiments, the second probe can comprise a spatial barcode, which is positioned 5' to the poly(GI) capture domain. In some embodiments, the spatial barcode in the first probe is different from the spatial barcode sequence in the second probe. In some embodiments, the spatial barcode in the first probe is the same as the spatial barcode sequence in the second probe.

In some embodiments, both the first and the second probes are cleavable. In some embodiments, the first probe and the second probe have different cleavage sites and are cleavable using different methods. In some embodiments, the first probe and the second probe have the same cleavable site and are cleavable using the same method. In some embodiments, the cleavage domain of the first probe is 5' to the poly(T) capture domain and/or the cleavage domain of the second probe is 5' to the poly(GI) capture domain.

In some embodiments, the first probe is not cleavable and the second probe is cleavable. In some embodiments, the cleavage site of the second probe is 5' to the poly(GI) capture domain of the second probe. In some embodiments, the cleavage site on the second probe is a uracil. In some embodiments, the uracil is cleaved by USER (Uracil-Specific Excision Reagent).

In some embodiments, the first probe further comprises a unique molecular identifier (UMI). In some embodiments, the second probe further comprises a unique molecular identifier (UMI). In some embodiments, the UMI in the first probe and the UMI in the second probe comprise different sequences. In some embodiments, the UMI in the first probe and the UMI in the second probe comprise the same sequence.

The 3' end of the second probe can be blocked by chemical modification, e.g., addition of an azidomethyl group as a chemically reversible capping moiety such that the probe does not include a free 3' end. Blocking or modifying the second probe, particularly at the free 3' end of the capture domain, prior to contacting the biological sample with the array, prevents modification of the second probe, e.g., prevents the addition of a poly(A) tail to the free 3' end of the second probe. Non-limiting examples of 3' modifications include dideoxy C-3' (3'-ddC), 3' inverted dT, 3' C3 spacer, 3' Amino, and 3' phosphorylation.

In some embodiments, the second probe includes a restriction endonuclease recognition sequence or a sequence of nucleotides cleavable by specific enzyme activities. For example, uracil sequences can be enzymatically cleaved from a nucleotide sequence using uracil DNA glycosylase (UDG) or Uracil Specific Excision Reagent (USER). As another example, other modified bases (e.g., modified by methylation) can be recognized and cleaved by specific endonucleases. The second probe can be subjected to an enzymatic cleavage, which removes the blocking domain and any of the additional nucleotides that are added to the 3' end of the capture probe during the modification process. Removal of the blocking domain reveals and/or restores the free 3' end of the second probe. In some embodiments, additional nucleotides can be removed to reveal and/or restore the 3' end of the second probe.

In some embodiments, a blocking domain can be incorporated into the second probe when it is synthesized, or after its synthesis. The terminal nucleotide of the capture domain is a reversible terminator nucleotide (e.g., 3'-O-blocked reversible terminator and 3'-unblocked reversible terminator), and can be included in the capture probe during or after probe synthesis.

"Adapter" refers to species that can be coupled to a polynucleotide sequence using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences. An adapter can include a sequencing primer sequence (e.g., R1 or a partial R1 ("pR1"), R2), or a flow cell attachment sequence (e.g., P5 or P7 or partial sequences thereof)).

Some embodiments of any of the methods described herein, step (h) includes sequencing all or a part of the sequence of the spatial barcode, or a complement thereof, and sequencing all of a part of the sequence of the target nucleic acid, or a complement thereof. The sequencing can be performed using any of the aforementioned methods. In some embodiments, step (h) includes sequencing the full-length sequence of the spatial barcode, or a complement thereof. In some embodiments, step (h) includes sequencing a part of the sequence of the spatial barcode, or a complement thereof. In some embodiments, step (h) includes sequencing the full-length sequence of the target nucleic acid, or a complement thereof. In some embodiments, step (h) includes sequencing a part of the target nucleic acid, or a complement thereof. In some embodiments, the sequencing is performed using high throughput sequencing. In some embodiments, the target nucleic acid is sequenced from the 5' end of the target nucleic acid. In some embodiments, the target nucleic acid is sequenced from the 3' end of the target nucleic acid. In some embodiments, the target nucleic acid is sequenced from both the 3' end and the 5' end of the target nucleic acid.

Figure 2:
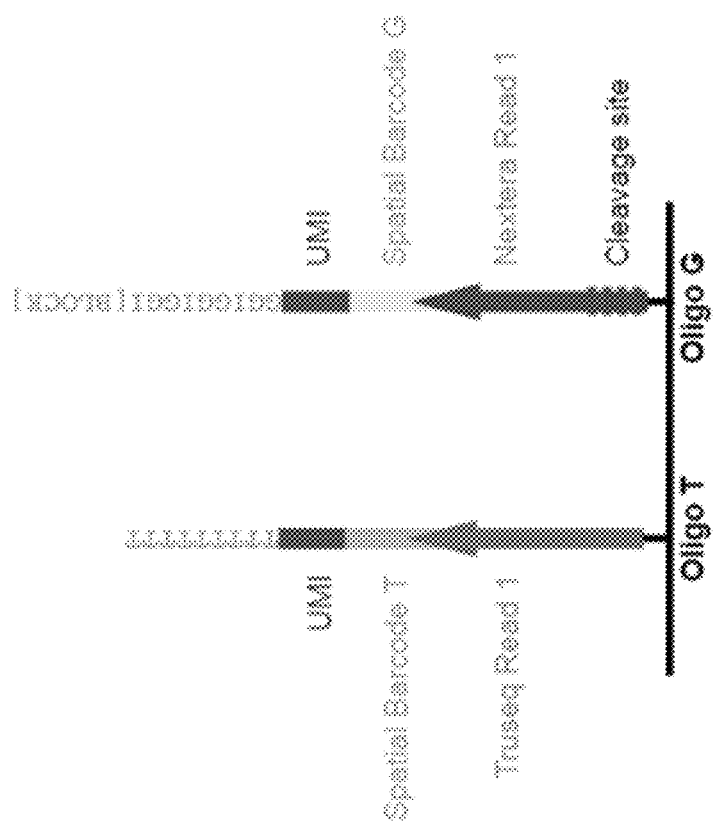
FIG. 2 is a schematic diagram showing an exemplary feature comprising an attached first probe and second probe.

FIG. 2 is a schematic diagram showing an exemplary feature comprising an attached first and second probe. The first probe comprises in a 5' to 3' direction: a functional domain comprising a Truseq Read 1 primer, a spatial barcode, a UMI, and a poly(T) capture domain, where the poly(T) capture domain binds specifically to the target nucleic acid. The 5' end of the first probe is attached to the feature.

The second probe comprises in a 5' to 3' direction: a cleavage domain, a functional domain comprising a Nextera Read 1 primer, a spatial barcode, a UMI, and a poly(GI) capture domain. The 5' end of the second probe is attached to the feature. In some embodiments, the poly(GI) capture domain comprises a sequence of (GGI)n, wherein n is about 3 to about 20. In some embodiments, the poly(GI) capture domain comprises a sequence of (GGI)n, wherein n is 1, 2, 3, 4, 5, 6, 7, 8, 9, 10, 11, 12, 13, 14, 15, 16, 17, 18, 19, or 20. In some embodiments, the 3' end of the second probe is reversibly blocked. The TruSeq and Nextera Read 1 primer sequences are used in Illumina sequencing workflows. However, it is understood that the present invention is not limited to any particular sequencing system, as such any primer or other functional sequences useful for other sequencing systems, as cited herein, can be equally used.

Figure 3A:
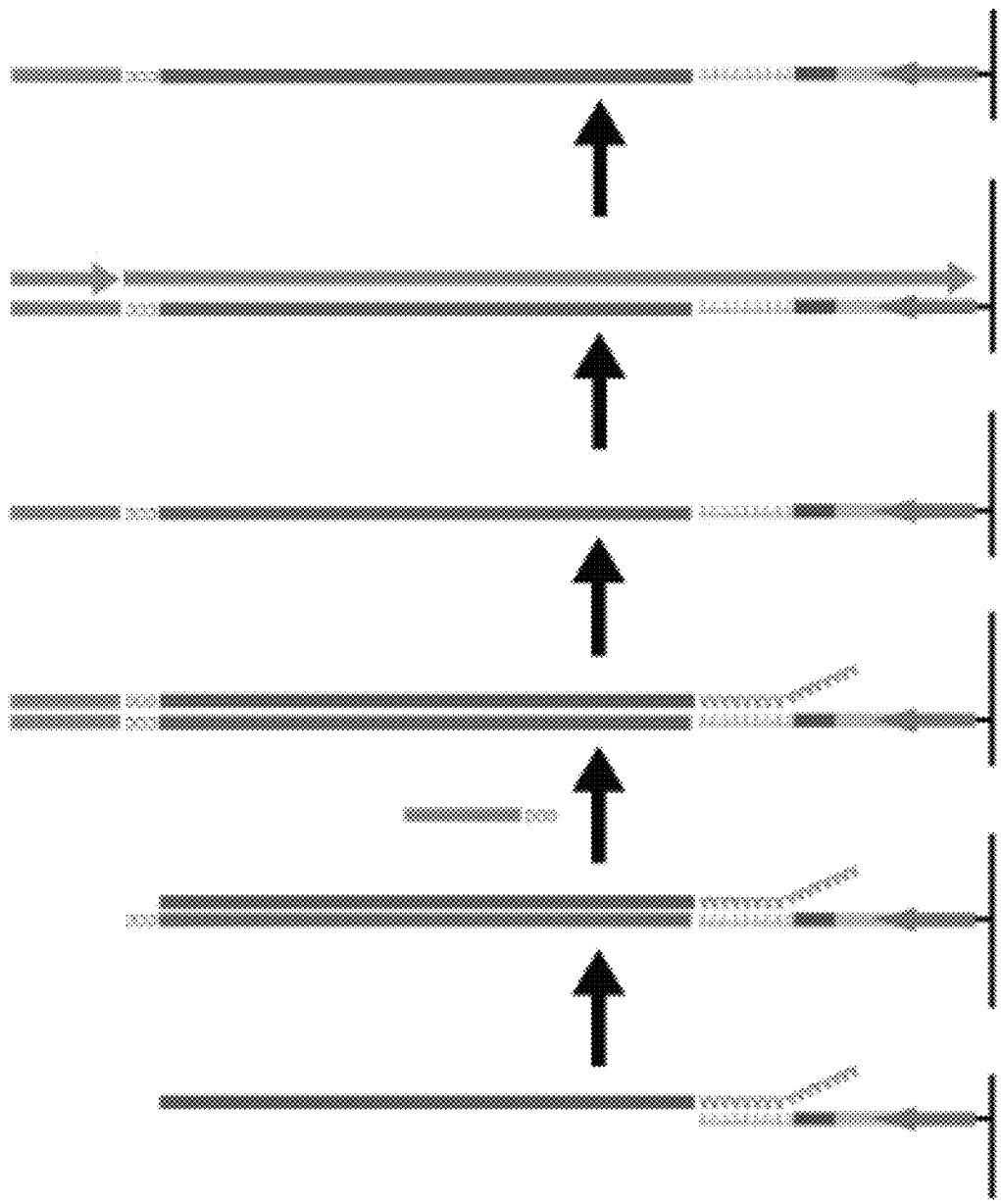
FIG. 3A-3C are workflow schematics illustrating exemplary steps for A) generating a spatially-barcoded sample for analysis and for use in further steps of the methods described herein (the first through the third step from the left show a captured nucleic acid comprising SEQ ID NO: 1), B) is a workflow schematic illustrating exemplary steps for generating a spatially-barcoded sample for analysis that allows for the sequencing of the target nucleic acid from both the 3' end and the 5' end (the second through the fourth steps, the sixth step, and the seventh step from the left show an extended first probe comprising SEQ ID NO: 2, and the fifth step from the left shows an extended first probe comprising SEQ ID NO: 3), and C) a schematic diagram showing an exemplary spatially-barcoded sample for analysis generated using the methods described herein.

FIG. 3A is an exemplary diagram showing, from left to right, the annealing of the target analyte (e.g., target nucleic acid) to the poly(T) capture domain of the first probe; the extension of the first probe to add a sequence that is complementary to a portion of the target nucleic acid; the ligation of an adaptor to the 5' end of the target nucleic acid specifically bound to the first probe; the addition of a sequence complementary to the adaptor to the 3' end of the first probe; the releasing of the target nucleic acid from the first probe; the generation of a complement of the extended first probe; and the releasing of the complement of the extended first probe. In some embodiments, the released target nucleic acid is sequenced. In some embodiments, the released complement of the extended first probe is sequenced.

Figure 3B:
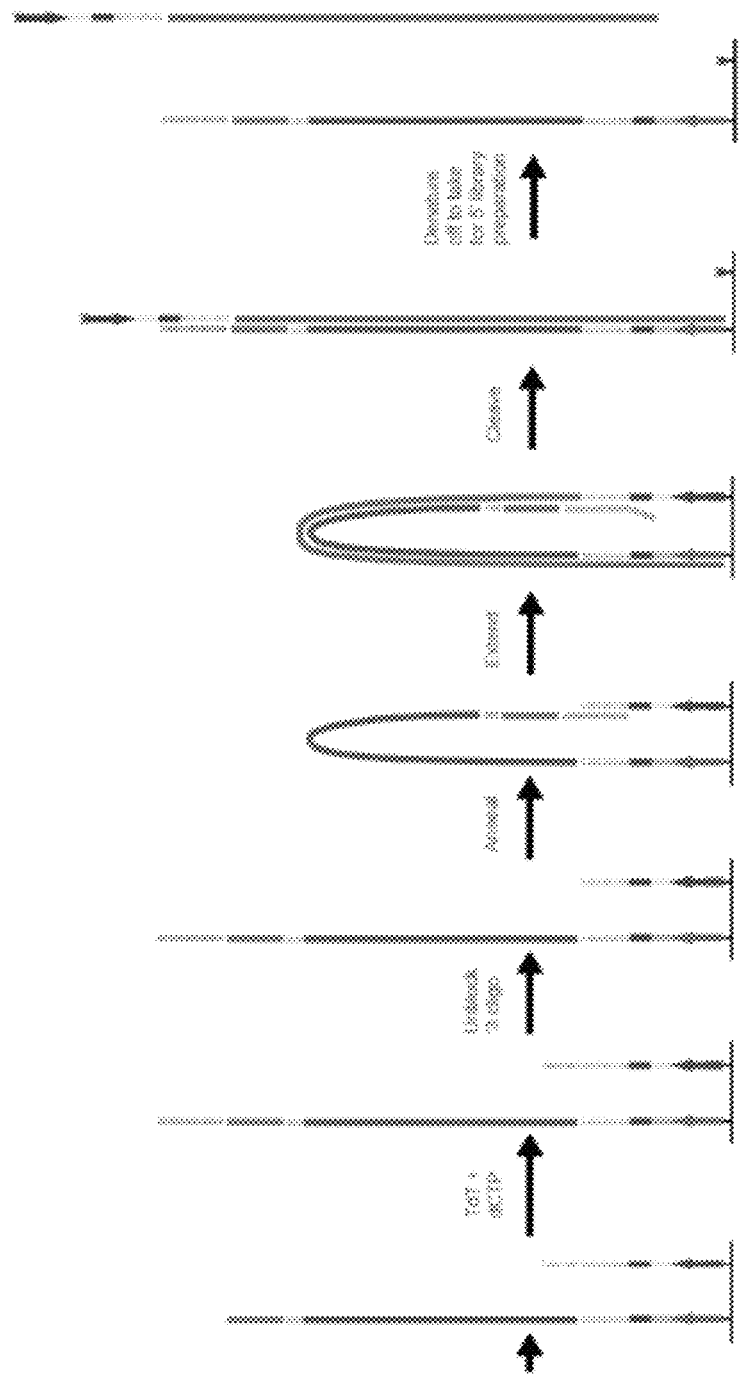

FIG. 3B is an exemplary diagram showing from left to right, the addition of non-templated cytosines to the 3' end of the extended first probe (e.g., extended to include a sequence that is complementary to a portion of the sequence of a target nucleic acid, and optionally, further comprising an adaptor sequence or a functional domain) to generate a poly(C) sequence, where the poly(C) sequence specifically binds to the poly(GI) capture domain of the second probe; the unblocking of the 3' end of the second probe; the hybridizing the poly(C) sequence on the first probe to the poly(GI) capture domain on the second capture probe; the extension of the 3' end of the second probe to add a sequence complementary to the extended first capture probe. The final step is the releasing of the extended second probe sequence from the feature. In alternative embodiments, the second probe comprises a poly(T) capture domain and a poly(A) sequence is added to the 3' end of the extended first probe (e.g., extended to add a sequence that is complementary to a portion of the sequence of a target nucleic acid), and the poly(A) sequence hybridizes to the poly(T) capture domain of the second probe.

Figure 3C:
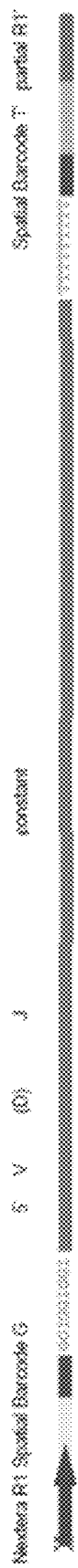

FIG. 3C is a schematic diagram showing an example of a sequence generated by the methods described herein. The exemplary sequence shown comprises, from 5' end to 3' end, the functional domain of the second probe, which comprises a sequencing primer; the spatial barcode of the second probe; the UMI sequence of the second probe; the poly(GI) sequence of the second probe; the target nucleic acid sequence (from 5' end to 3' end); a sequence complementary to the UMI sequence of the first probe; a sequence complementary to the spatial barcode of the first probe; and a sequence complementary to part or the full sequence of the functional domain of the first probe, which comprises a sequencing primer. In some embodiments, the two sequencing primers have the same sequence. In some embodiments, the two sequencing primers have different sequences.

Further steps of the methods described herein include, for example, determining (i) all or a part of the sequence of the spatial barcode on either end of the sequence depicted in FIG. 3C, or a complement thereof, and (ii) all or a part of the sequence of the target nucleic acid, or a complement thereof, and using the sequences of (i) and (ii) to determine the location of the target nucleic acid in the biological samples.

The methods described herein allows for the sequencing of the target nucleic acid from either the 3' end or the 5' end, or both the 3' and the 5' ends of the target nucleic acid. For target nucleic acids that have large sizes (e.g., larger than 1 kb), the methods allow more accurate spatial sequence information to be obtained.

III. Arrays for Making 5' Libraries or VDJ Libraries

Also described herein is an array comprising a feature, where the feature comprises an attached first and second probe, wherein: a 5' end of the first probe is attached to the feature; the first probe comprises in a 5' to a 3' direction: a spatial barcode and a poly(T) capture domain, wherein the poly(T) capture domain binds specifically to the target nucleic acid; a 5' end of the second probe is attached to the feature; a 3' end of the second probe is reversibly blocked; and the second probe comprises a poly(GI) capture domain.

In some embodiments of any of the arrays described herein, a feature can include two or more pairs of a first and a second probe (e.g., any of the first and second probes described herein). A first pair of a first and a second probe at a feature, as compared to a second pair of a first and a second probe at the feature, can have a different first and/or second probe as compared to first and/or second probe of the second pair (e.g., a different capture domain in the first probe and/or a different barcode in the first and/or second probes). In some embodiments of any of the arrays described herein, the spatial barcode in the first probe of the first pair and the spatial barcode in the first probe of the second pair are the same. In some embodiments of any of the arrays described herein, the spatial barcode in the first probe of the first pair and the spatial barcode in the first probe of the second pair are different. In some embodiments of any of the arrays described herein, the capture domain of the first probe of the first pair is the same as the capture domain of the first probe of the second pair. In some embodiments of any of the arrays described herein, the capture domain of the first probe of the first pair is different from the capture domain of the first probe of the second pair.

In some embodiments of any of the arrays described herein, the capture domain on the first probe has a poly(T) capture domain, where the poly(T) capture domain is configured to interact with a target nucleic acid (e.g., positioned at the 3' end of the first probe). For example, the poly(T) capture domain specifically binds to a messenger RNA (mRNA), via the poly(A) tail of the mRNA. For example, a poly(T) capture domain can include at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30 contiguous thymidines.

In some embodiments of any of the arrays described herein, the poly(GI) capture domain comprises a sequence of at least 5 contiguous guanosine(s) and/or inosine(s). For example, a poly(GI) capture domain comprises a sequence of (GGI)n, wherein n is about 3 to about 20. In some embodiments, the poly(GI) capture domain comprises a sequence of (GGI)n, wherein n is 1, 2, 3, 4, 5, 6, 7, 8, 9, 10, 11, 12, 13, 14, 15, 16, 17, 18, 19, or 20. For example, a poly(GI) capture domain comprises a sequence of (GI)n, wherein n is about 4 to about 30. For example, a poly(GI) capture domain comprises a sequence of (GI)n, wherein n is 4, 5, 6, 7, 8, 9, 10, 11, 12, 13, 14, 15, 16, 17, 18, 19, 20, 21, 22, 23, 24, 25, 26, 27, 28, 29, or 30. For example, a poly(GI) capture domain comprises a sequence of (GI)n, wherein n is about 4 to about 30. For example, a poly(GI) capture domain comprises a sequence of (GI)n, wherein n is 4, 5, 6, 7, 8, 9, 10, 11, 12, 13, 14, 15, 16, 17, 18, 19, 20, 21, 22, 23, 24, 25, 26, 27, 28, 29, or 30.

In some embodiments of any of the arrays described herein, the second probe can comprise a spatial barcode, which is positioned 5' to the poly(GI) capture domain. In some embodiments, the spatial barcode in the first probe is different from the spatial barcode sequence in the second probe. In some embodiments, the spatial barcode in the first probe is the same as the spatial barcode sequence in the second probe.

In some embodiments of any of the arrays described herein, both the first and the second probes are cleavable. In some embodiments, the first probe and the second probe have different cleavage sites and are cleavable using different methods. In some embodiments, the first probe and the second probe have the same cleavable site and are cleavable using the same method. In some embodiments, the cleavage domain of the first probe is 5' to the poly(T) capture domain and/or the cleavage domain of the second probe is 5' to the poly(GI) capture domain.

In some embodiments of any of the arrays described herein, the first probe is not cleavable and the second probe is cleavable. In some embodiments, the cleavage site of the second probe is 5' to the poly(GI) capture domain of the second probe. In some embodiments, the cleavage site on the second probe is a uracil. In some embodiments, the uracil is cleaved by USER (Uracil-Specific Excision Reagent).

In some embodiments of any of the arrays described herein, the first probe further comprises a unique molecular identifier (UMI). In some embodiments, the second probe further comprises a unique molecular identifier (UMI). In some embodiments, the UMI in the first probe and the UMI in the second probe comprise different sequences. In some embodiments, the UMI in the first probe and the UMI in the second probe comprise the same sequence.

In some embodiments of any of the arrays or methods described herein, the first and/or second probe can further include a functional domain (e.g., a sequencing handle). In some embodiments, the first and second probe comprise a functional domain. In some embodiments, the functional domain the first and second probes is the same. In some embodiments, the functional domain in the first probe and the functional domain in the second probe are different.

Target Nucleic Acids

Described herein are methods for determining a location of a target nucleic acid in a biological sample. Examples of target nucleic acids include DNA (such as genomic DNA, methylated DNA, specific methylated DNA sequences, or fragmented DNA), RNA such as various types of coding and non-coding RNA. Examples of the different types of RNA analytes include messenger RNA (mRNA), ribosomal RNA (rRNA), transfer RNA (tRNA), and microRNA (miRNA).

In some embodiments, the target nucleic acid encodes a T-cell receptor (TCR), found on the surface of T lymphocytes (e.g., T cells). T-lymphocytes play a role in a body's immune response. TCR is a transmembrane heterodimer consisting of an alpha and beta chain or a delta and gamma chain linked by a disulfide bond. Within these chains are complementary determining regions (CDRs) which determine the antigen to which the TCR will bind. TCRs activate the T cells in which they are expressed leading to different immune responses.

TCR development occurs through a lymphocyte specific process of gene recombination, which assembles a final sequence from a large number of potential segments. This genetic recombination of TCR gene segments in somatic T cells occurs during the early stages of development in the thymus. The TCRα gene locus contains variable (V) and joining (J) gene segments (Vβ and Jβ), whereas the TCRβ locus contains a diversity (D) gene segment in addition to Vα and Jα segments. Accordingly, the α chain is generated from VJ recombination and the β chain is involved in VDJ recombination. This is similar for the development of γδ TCRs, in which the TCRγ chain is generated from VJ recombination and the TCR gene is generated from VDJ recombination.

The TCRα chain gene locus consists of 46 variable segments, 8 joining segments. and the constant region. The TCR β chain gene locus consists of 48 variable segments followed by two diversity segments, 12 joining segments, and two constant regions. The D and J segments are located within a relatively short 50 kb region while the variable genes are spread over a large region of 1.5 mega bases (TCRα) or 0.67 megabases (TCRβ). The methods described herein allow for the spatial identification and analysis of rearranged V(D)J TCR sequences from both the 3' end and the 5' end.

In some embodiments, the target nucleic acid encodes a full-length rearranged V(D)J TCR. In some embodiments, the target nucleic acid encodes a part of a rearranged V(D)J TCR. In some embodiments, the target nucleic acid encodes one or more (e.g., one, two, or three) full-length complementarity determining region(s) (CDR(s)) of the TCR. In some embodiments, the target nucleic acid encodes a part of a complementarity determining region (CDR) of the TCR.

In some embodiments, the target nucleic acid encodes an engineered TCR, for example, a recombinant TCR used in immunotherapy (e.g., an adoptive cell therapy). In some embodiments, the TCR may be αβ heterodimers or may be a single-chain TCR. Single chain TCRs include αβ TCR polypeptides of the Vα-L-V β, Vβ-L-Vα, Vα-Cα-L-Vβ, or Vα-L-Vβ-C β types, where Vα and Vβ are TCR α and β variable regions respectively, Cα and Cβ are TCR α and β constant regions respectively, and L is a linker sequence. In some embodiments, the TCR does not have transmembrane or cytoplasmic domains.

In some embodiments, the target nucleic acid encodes a chimeric antibody receptor (CAR).

In some embodiments, the target nucleic of interest encodes a B-cell receptor (BCR), found on the surface of B lymphocytes (e.g., B cells). B lympochytes also play a role in a body's immune response. A BCR is a transmembrane protein composed of an immunoglobulin molecule and a signal transduction moiety, or a heterodimer CD79. In some embodiments, the target nucleic acid encodes a heavy chain or light chain of an immunoglobulin (e.g., IgM, IgG, IgA, IgD, and IgE). In some embodiments, the target nucleic acid encodes an immunoglobulin heavy chain. In some embodiments, the target nucleic acid encodes an immunoglobulin light chain. In some embodiments, the target nucleic acid encodes one or more (e.g., one, two, or three) full-length complementarity determining region(s) (CDR(s)) of an immunoglobulin. In some embodiments, the target nucleic acid encodes a part of a complementarity determining region (CDR) of the immunoglobulin.

In some embodiments, the immunoglobulin can be an engineered immunoglobulin. In some embodiments, the immunoglobulin is a fragment of a full-length immunoglobulin, e.g., a single-chain variable fragment. In some embodiments, the immunoglobulin is a single domain antibody (sdAb).

The size of the target nucleic acid can be any suitable size of a nucleic acid molecule in a biological sample. In some embodiments, the size of the target nucleic acid is about 50 nucleotides to about 100,000 nucleotides (e.g., about 50 nucleotides to about 50,000 nucleotides, about 200 nucleotides to about 10,000 nucleotides, about 500 nucleotides to about 8,000 nucleotides, about 500 nucleotides to about 2,000 nucleotides, about 500 nucleotides to about 1,000 nucleotides, about 1,000 nucleotides to about 8,000 nucleotides, about 1,000 nucleotides to about 4,000 nucleotides, about 1,000 nucleotides to about 2,000 nucleotides, about 2,000 nucleotides to about 4,000 nucleotides, about 4,000 nucleotides to about 6,000 nucleotides, about 6,000 nucleotides to about 8,000 nucleotides, about 8,000 nucleotides to about 10,000 nucleotides).

IV. Capture and Analysis of 5' Polynucleotide Sequences

Methods are provided for detecting, determining location of, and/or sequencing 5' sequences of polynucleotides. The methods include capturing a polynucleotide with a first probe (e.g., binding, ligating, or hybridizing a polynucleotide to a probe). The first probe contains a first capture domain to which a polynucleotide of interest (e.g., a target polynucleotide sequence of a biological analyte, e.g., within a biological sample) binds. In one embodiment, the target polynucleotide binds to (e.g., hybridizes with) a complementary or partially complementary sequence of the first capture domain. In some embodiments, the first probe contains one or more barcode sequences (e.g., a spatial barcode or a cell barcode sequence), e.g., 5' to the capture domain. The first probe may contain an extendible 3' end, e.g., at the 3' end of the capture domain. In one embodiment, the 5' end of the first capture probe is attached to a substrate.

In some embodiments, a target polynucleotide binds or attaches to the first capture domain of the first probe. In one embodiment, the target polynucleotide contains a sequence that is complementary or partially complementary to a sequence of the first probe, and the target polynucleotide hybridizes to the complementary or partially complementary sequence of the first probe.

The 3' end of the first probe may be extended to generate a first extension product (e.g., a cDNA sequence) that includes a nucleotide sequence that is complementary to the target polynucleotide sequence or a portion thereof. The first extension product can bind to a second probe or to one or more nucleotide(s) attached to a substrate.

In some embodiments, an adapter is attached to the 3' end of the first extension product. The adapter or a 3' sequence thereof may be complementary to a sequence (e.g., a second capture domain) of a second probe. In one embodiment, the adapter is ligated to the 3' end of the first extension product. In another embodiment, a template switching oligonucleotide (TSO) binds (e.g., hybridizes) to untemplated nucleotides that are added to the 3' end of the first extension product. The 3' end of the TSO is then extended to generate an adapter that is complementary to the TSO. The untemplated nucleotides may be A, T, C, and/or G nucleotides, or any sequence thereof. In some embodiments, the untemplated nucleotides are a poly(C) or poly(G) sequence. In one embodiment, the untemplated nucleotides are a poly(C) sequence and the TSO includes a 3' poly(G) sequence. In another embodiment, the untemplated nucleotides are a poly(G) sequence and the TSO includes a 3' poly(C) sequence.

In some embodiments, the first extension (e.g., cDNA) product, generated from extension of the first probe bound to the target polynucleotide sequence, binds to a second capture domain of a second probe. In some embodiments, the second capture domain may include: a 3' sequence that is complementary to a 3' adapter, or a portion thereof, of the first extension product. The adapter binds (e.g., hybridizes) to the 3' complementary sequence, and then a 3' end of the second capture domain is extended to produce a second extension product. The second extension product includes a sequence that is complementary to the 5' sequence of the first extension product, e.g., includes a 5' sequence of the target polynucleotide, proximal to the sequence of the second capture domain. In one embodiment, the 5' end of the second probe is attached to a substrate. In some embodiments, the second probe may be cleaved, e.g., at a site 5' to the second capture domain, thereby releasing the second probe from the substrate, and the released second probe may be used, for example, for amplification and/or sequencing.

In other embodiments, the first extension (e.g., cDNA) product, generated from extension of the first probe bound to the target polynucleotide sequence, is ligated to a second probe. For example, the 3' end of the first extension product may be ligated to a 5' end of the second probe. In some embodiments, a splint oligonucleotide binds (e.g., hybridizes) to a 5' sequence of the second probe and to a 3' sequence of the first extension product. The 5' end of the second probe is ligated to the 3' end of the first extension product, and the 3' end of the splint oligonucleotide is extended to produce a second extension product. The second extension product includes a sequence that is complementary to the 5' sequence of the first extension product, e.g., includes a 5' sequence of the target polynucleotide, proximal to the sequence of the second capture domain. In one embodiment, the 3' end of the second probe is attached to a substrate.

The method may further include detection of the target polynucleotide, for example, by binding a detectable label, such as a fluorescent label, to the second extension product.

In the methods described herein, the first and/or second extension product may be used for preparation of a 3' and/or 5' sequencing library, respectively.

The method may further include determining the sequence of all or a portion of the target polynucleotide sequence, such as the sequence of at least a 5' portion of the target polynucleotide sequence. In some embodiments, prior to sequencing, an amplification product may be generated from the second extension product, wherein the amplification product includes a 5' sequence of the target polynucleotide or a complement thereof, and the amplification product may be used for sequencing.

The first and/or second probe may contain a barcode sequence (e.g., a spatial barcode or a cell barcode sequence). In some embodiments, the first and second probes contain barcode sequences, which may be the same or different. In some embodiments, the first and/or second probe contains a unique molecular identifier (UMI). In some embodiments, the UMI in the first probe and the UMI in the second probe comprise different sequences.

In other embodiments, a nucleotide or a sequence of nucleotides is bound at the 3' end to a substrate, and the 3' end of the first extension product is bound to a 5' end of the nucleotide(s), for example via hybridization or ligation. In some embodiments, a splint oligonucleotide binds (e.g., hybridizes) to a 5' end of the nucleotide(s) and to a 3' sequence of the first extension product. The 5' end of the nucleotide(s) is ligated to the 3' end of the first extension product, and the 3' end of the splint oligonucleotide is extended to produce a second extension product. The second extension product includes a sequence that is complementary to the 5' sequence of the first extension product, e.g., includes a 5' sequence of the target polynucleotide, proximal to the sequence of the second capture domain.

The first and/or second extension product may be produced using a polymerase, e.g., a DNA polymerase (RNA-dependent DNA polymerase (e.g., reverse transcriptase) or a DNA-dependent DNA polymerase), or an RNA polymerase.

The target polynucleotide may comprise or consist of DNA or RNA, and/or may contain non-natural nucleotides. The first capture domain may include a poly(dT) sequence, a random sequence, or a sequence that is complementary or partially complementary to a target sequence of interest. In certain embodiments, the target polynucleotide is mRNA. The mRNA may encode, for example, a TCR or a B-cell receptor (BCR), and in some embodiments, the method may include determining a sequence that encodes one or more complementarity determining region(s) (CDR(s)) of the TCR or BCR. The mRNA may encode, for example, an immunoglobulin heavy chain or light chain, and the method may include determining a sequence that encodes one or more CDR(s) of the immunoglobulin heavy chain or light chain.

In some embodiments, the target nucleic acid encodes a full-length rearranged V(D)J TCR. In some embodiments, the target nucleic acid encodes a portion of a rearranged V(D)J TCR. In some embodiments, the target nucleic acid encodes one or more (e.g., one, two, or three) full-length complementarity determining region(s) (CDR(s)) of the TCR. In some embodiments, the target nucleic acid encodes a part of a complementarity determining region (CDR) of the TCR.

In some embodiments, the target nucleic acid encodes an engineered TCR, for example, a recombinant TCR used in immunotherapy (e.g., an adoptive cell therapy). In some embodiments, the TCR may be αβ heterodimers or may be a single-chain TCR. Single chain TCRs include αβ TCR polypeptides of the Vα-L-Vβ, Vβ-L-Vα, Vα-Cα-L-Vβ, or Vα-L-Vβ-C β types, where Vα and Vβ are TCR α and β variable regions respectively, Cα and Cβ are TCR α and β constant regions respectively, and L is a linker sequence. In some embodiments, the TCR does not have transmembrane or cytoplasmic domains.

In some embodiments, the target nucleic acid encodes a chimeric antibody receptor (CAR).

In some embodiments, the target nucleic acid encodes a heavy chain or light chain of an immunoglobulin (e.g., IgM, IgG, IgA, IgD, and IgE). In some embodiments, the target nucleic acid encodes an immunoglobulin heavy chain. In some embodiments, the target nucleic acid encodes an immunoglobulin light chain. In some embodiments, the target nucleic acid encodes one or more (e.g., one, two, or three) full-length complementarity determining region(s) (CDR(s)) of an immunoglobulin. In some embodiments, the target nucleic acid encodes a part of a complementarity determining region (CDR) of the immunoglobulin.

In some embodiments, the immunoglobulin can be an engineered immunoglobulin. In some embodiments, the immunoglobulin is a fragment of a full-length immunoglobulin, e.g., a single-chain variable fragment. In some embodiments, the immunoglobulin is a single domain antibody (sdAb).

In some embodiments, the target polynucleotide includes a genetic variation, such as an isoform, a splice variant, or a single nucleotide polymorphism (SNP), e.g., in a 5' region of the mRNA, and the method includes detection and/or sequencing of the genetic variation. For example, the first capture domain may include a sequence that is specific for the genetic variation, such as a sequence that binds to a change in a nucleic acid or protein (e.g., a mutation or SNP.

The biological sample from which the target polynucleotide is derived may be, for example, a tissue section, a primary cell, a cell line, or an organoid. In some embodiments, the method includes permeabilizing the biological sample, to release a biological analyte, prior to contacting the first probe with the target polynucleotide sequence of the biological analyte. In some embodiments, the biological sample is a tissue section, such as a fixed (e.g., formalin-fixed and paraffin-embedded (FFPE) or paraformaldehyde (PFA)) tissue section, or a fresh frozen tissue section.

In some embodiments, the first and second probes are attached to a substrate (a support), such as a substrate that comprises an array. The array may be, for example, a bead array or a slide. For example, the first and second probes may be attached to a feature in an array. The ratio of first probes to second probes may be about 1:1000 to about 1000:1, or about 1:1 to about 1:100. The first and second probes may be attached directly or indirectly to the substrate. In some embodiments, the first and second probes are attached indirectly to the substrate, such as attached to beads (for example, gel beads) that are attached to the substrate. In some embodiments, the first and second probes are attached indirectly to the substrate via a linker (for example, a cleavable linker such as photocleavable linker (e.g., bromodeoxyuridine (BrdU), an enzymatic linker (e.g., uracil specific excision enzyme), or a chemical linker (e.g., a sulfhydryl, amide or carboxyl group), that are attached to the substrate.

An exemplary, non-limiting workflow is depicted in FIGS. 4A-4J. In the workflow depicted in FIGS. 4A-4J, presence and/or location (e.g., spatial location) of a biological analyte may be determined and/or a 5' sequence (e.g., sequence of a 5' region) of a polynucleotide sequence of a biological analyte may be detected and/or determined. A "5' region" refers to a sequence that is at or near the 5' end of a polynucleotide sequence, or a sequence that is closer in proximity to the 5' end than the 3' end of a polynucleotide sequence. A biological sample is contacted with a substrate 401. The substrate includes an attached first probe 402 and an attached second probe 403. (FIG. 4A) In one embodiment, the first probe 402 includes, in a 5'-3' direction: a barcode (e.g., spatial barcode); a first capture domain; and a 3' end. In the embodiment depicted in FIGS. 4A-4J, the second probe 403 includes a second capture domain and a 3' end, and both the first probe 402 and the second probe 403 are attached at their 5' ends to the substrate 401.

A biological sample is contacted with the substrate 401 and a target polynucleotide sequence 404 of a biological analyte binds (e.g., hybridizes) to the first capture domain of the first probe 402. (FIG. 4B) In some instances, the first capture domain includes a sequence specific for an RNA molecule. In some instances, the first capture domain includes a poly-T sequence. In some instances, the first capture domain includes a sequence complementary to a region of an immune molecule, such as the constant region of a TCR or BCR sequence (as described herein). In some instances, the first capture domain includes a sequence complementary to a region of an immunoglobulin molecule, such as one or more CDRs of an immunoglobulin heavy or light chain.

Figure 4E:
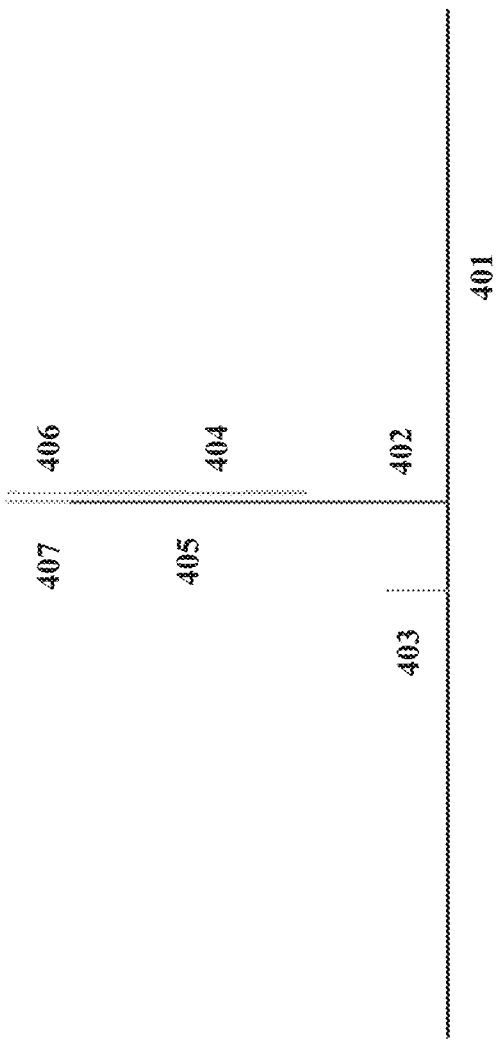
Figure 4F:
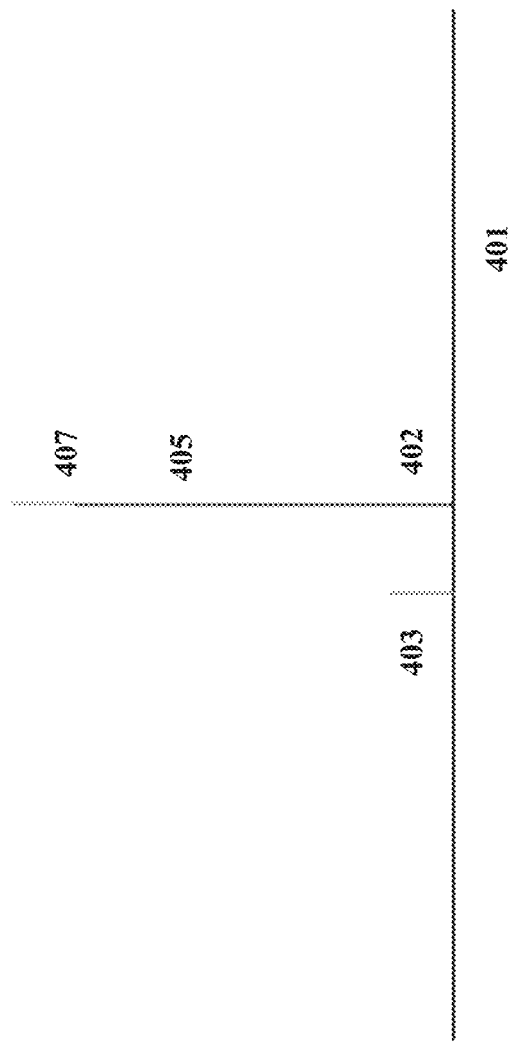
Figures 4I, 4J:
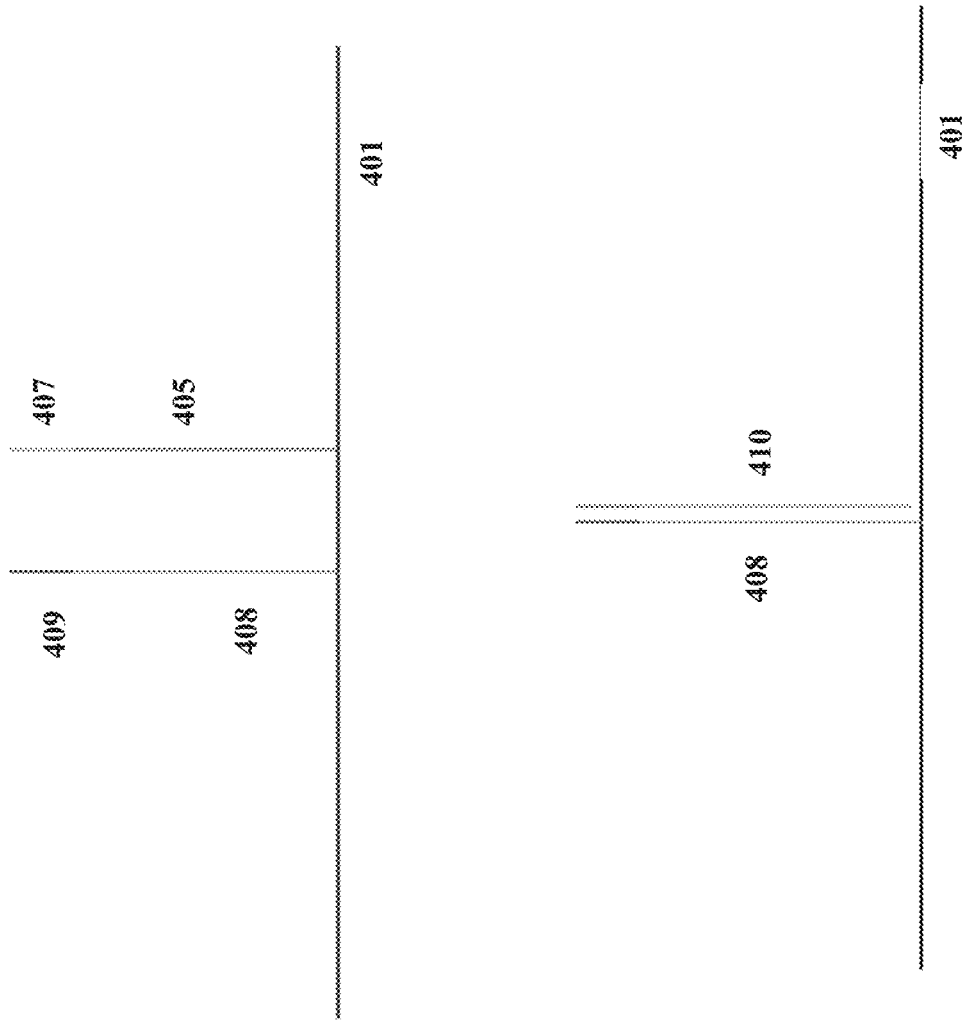

The 3' end of the first probe 402 is extended to produce a first extension product 405. (FIG. 4C) An adapter is attached to the 3' end of the first extension product 405. In one embodiment, depicted in FIG. 4D, untemplated nucleotides are added to the 3' end of the first extension product 405. A template switching oligonucleotide (TSO) 406 binds (e.g., hybridizes) to the untemplated nucleotides, and then the 3' end of the first extension product is extended, producing a polynucleotide sequence 407 that is complementary to the TSO sequence. (FIG. 4E). The target polynucleotide sequence 404 and TSO 406 are stripped away (e.g., denatured). (FIG. 4F)

In the embodiment depicted in FIG. 4G, the second capture domain of the second probe 403 includes a sequence that is complementary to the adapter 407, i.e., the second capture domain contains the TSO sequence or a partial sequence thereof. The adapter 407 at the 3' end of the first extension product 405 binds to the second capture domain at the 3' end of the second probe 403. The 3' end of the second probe 403 is extended, producing a second extension product 408, which includes a 3' sequence that is complementary to the sequence of the first probe or a portion thereof 409. (FIG. 4H) The first extension product 405 with 3' adapter 407 includes a 3' sequence complementary to the target polynucleotide proximal to the first capture domain sequence, and may be used for preparation of a 3' sequence library; and/or the second extension product 408 with 3' sequence complementary to the first probe 407 includes a 5' sequence of the target polynucleotide proximal to the second capture domain, and may be used for preparation of a 5' sequence library. (FIG. 4I) In one embodiment, depicted in FIG. 4J, a copy 410 of the second extension product (e.g., amplification product) 408 is produced. The first and/or second extension product, and/or copy (e.g., amplification product thereof) may be detected and/or sequenced, and the resulting information obtained may be used to determine presence and/or location (e.g., spatial location) of the biological analyte in the biological sample.

Figure 5:
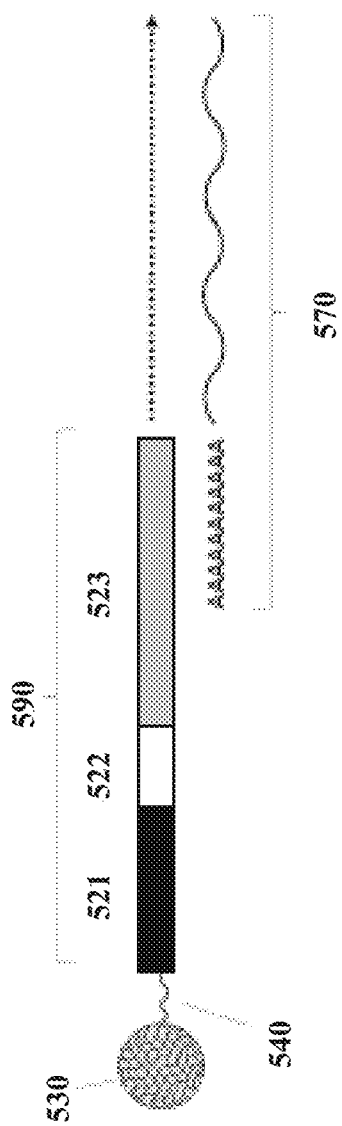
FIG. 5 depicts an exemplary workflow for analysis of one or more analyte(s) from single cells. A captured nucleic acid comprising SEQ ID NO: 4 is shown.

In some embodiments of the method, analysis of one or more analyte(s) from single cells is performed according to an exemplary, nonlimiting workflow as depicted in FIG. 5. Single cells and supports 530 (e.g., a bead, such as a gel bead) including a nucleic acid barcode molecule 590 are co-partitioned into a partition amongst a plurality of partitions (e.g., a droplet of a droplet emulsion or a well of a micro/nanowell array). In some instances, the partition includes at most a single cell and a single support 530. In some embodiments, nucleic acid barcode molecule 590 is attached to support 530 via a releasable linkage 540 (e.g., including a labile bond). Upon release of nucleic acid barcode molecule 590 from the support 530, barcoded molecules may be generated within the partition. In some embodiments, nucleic acid barcode molecule 590 includes a sequence 523 complementary to a sequence of RNA molecule 560 from a cell. In some instances, sequence 523 includes a sequence specific for an RNA molecule. In some instances, sequence 523 includes a poly-T sequence. In some instances, sequence 523 includes a sequence complementary to a region of an immune molecule, such as the constant region of a TCR or BCR sequence (as described herein). In some instances, sequence 523 includes a sequence complementary to a region of an immunoglobulin molecule, such as one or more CDRs of an immunoglobulin heavy or light chain. Sequence 523 is bound (e.g., hybridized) to RNA molecule 560 and a cDNA molecule 570 is generated in a reverse transcription reaction, generating a barcoded nucleic acid molecule including cell (e.g., partition specific) barcode sequence 522 (or a reverse complement thereof) and a sequence of cDNA 570 (or a portion thereof). Barcoded nucleic acid molecules can then be optionally processed as described elsewhere herein, e.g., to amplify the molecules and/or append sequencing platform specific sequences to the fragments. See, e.g., U.S. Pat. Pub. Nos. 2018/0105808 and 2019/0367969 and U.S. Pat. Nos. 10,273,541, 10,480,029, and 10,550,429, each of which is hereby incorporated by reference in its entirety. Barcoded nucleic acid molecules, or derivatives generated therefrom, can then be sequenced on a suitable sequencing platform.

V. Methods for Removal of a Polynucleotide Region from a Template Polynucleotide Methods are provided for detecting a biological analyte in a biological sample, wherein sequences that are not of interest are removed from a template polynucleotide to facilitate analysis. The methods include binding (e.g., hybridizing) first and second oligonucleotides to a template polynucleotide. The template polynucleotide includes a polynucleotide sequence of a biological analyte or the complement thereof. In some embodiments, the template polynucleotide includes a barcode sequence 5' to the polynucleotide sequence of the biological analyte, (e.g., a spatial barcode sequence or a cell barcode sequence). The first oligonucleotide includes a sequence that is complementary to a first sequence of the template polynucleotide, and a 3' end. The second oligonucleotides is a bridging oligonucleotide that includes sequences that are complementary to second and third sequences of the template polynucleotide, wherein the second and third sequences are flanking a polynucleotide region of the template polynucleotide to be removed. In some embodiments, the second oligonucleotide includes a 5' phosphate group. The first sequence of the template polynucleotide is 3' to the second sequence of the template polynucleotide. The second and third sequences of the template polynucleotide are 3' and 5', respectively, to a fourth sequence of the template polynucleotide which is a polynucleotide region to be removed.

The 3' end of at least the first oligonucleotide is extended. In some embodiments, 3' ends of both the first and second oligonucleotides are extended. In one embodiment, a non-strand displacing, non 5'-3' exonuclease DNA polymerase is used for oligonucleotide extension. For example, T4 and T7 DNA polymerases (e.g., NEB catalog numbers 0203 and 0274) lack strand displacement activity and can be used. The first oligonucleotide is extended to the 5' end of the second oligonucleotide, and then joined to the second oligonucleotide. In some embodiments, the 3' end of the first oligonucleotide is ligated to a phosphate group at the 5' end of the second oligonucleotide. The resulting polynucleotide product includes the complement of 5' and 3' portions of the template polynucleotide sequence, and does not include the complement of the fourth sequence of the template polynucleotide.

In some embodiments, prior to binding the first and second oligonucleotides to the template polynucleotide, the template polynucleotide is captured from a biological sample. For example, a biological sample may be contacted with a probe. The probe may include, in a 5' to 3' direction, a barcode sequence (e.g., a spatial barcode sequence or a cell barcode sequence), a capture domain. In some embodiments, the probe includes a unique molecular identifier (UMI).

The biological sample is contacted with the probe where a target polynucleotide sequence of a biological analyte (a template polynucleotide) binds (e.g., hybridizes) to the capture domain. A 3' end of the capture domain is extended, generating an extension product that includes a sequence that is complementary to the template polynucleotide, or a portion thereof (e.g., a cDNA extension product). The first and second oligonucleotides then bind to the extension product, are extended, as described above, and the 3' end of the extended first oligonucleotide is joined to the 5' end of the extended second oligonucleotide. The first oligonucleotide is complementary to a first sequence of the extension product, and the second oligonucleotide is complementary to second and third sequences of the extension product. The first sequence of the extension product is 3' to the second sequence of the extension product, and the second and third sequences are 3' and 5', respectively, to a fourth sequence of the extension product, which is to be removed. The polynucleotide product does not include the complement of the fourth sequence of the extension product (i.e., the sequence of the template polynucleotide to which the fourth sequence of the extension product is complementary). In one embodiment, uridine residues are incorporated into the extension product, and the method includes digestion of the extension product with a uracil specific excision reagent (USER), after oligonucleotide extension and joining of the extended first oligonucleotide to the second oligonucleotide.

In some embodiments, the polynucleotide region to be removed (e.g., the fourth sequence of a template polynucleotide or the complement thereof) is about 10 nucleotides to about 1000 nucleotides, or longer. For example, the fourth sequence may be any of about 10 nucleotides to about 100 nucleotides about 75 nucleotides to about 125 nucleotides, about 125 nucleotides to about 175 nucleotides, about 175 nucleotides to about 225 nucleotides, about 225 nucleotides to about 275 nucleotides, about 275 nucleotides to about 325 nucleotides, about 325 nucleotides to about 375 nucleotides, about 375 nucleotides to about 425 nucleotides, about 425 nucleotides to about 475 nucleotides, about 475 nucleotides to about 525 nucleotides, about 525 nucleotides to about 575 nucleotides, about 575 nucleotides to about 625 nucleotides, about 625 nucleotides to about 675 nucleotides, about 675 nucleotides to about 725 nucleotides, about 725 nucleotides to about 775 nucleotides, about 775 nucleotides to about 825 nucleotides, about 825 nucleotides to about 875 nucleotides, about 875 nucleotides to about 925 nucleotides, about 925 nucleotides to about 975 nucleotides, about 950 nucleotides to about 1000 nucleotides, about 20 nucleotides to about 200 nucleotides, about 50 nucleotides to about 150 nucleotides, about 100 nucleotides to about 200, nucleotides about 150 nucleotides to about 250 nucleotides, about 200 nucleotides to about 300 nucleotides, about 250 nucleotides to about 350 nucleotides, about 300 nucleotides to about 400 nucleotides, about 350 nucleotides to about 450 nucleotides, about 400 nucleotides to about 500 nucleotides, about 450 nucleotides to about 550 nucleotides, about 500 nucleotides to about 600 nucleotides, about 550 nucleotides to about 650 nucleotides, about 600 nucleotides to about 700 nucleotides, about 650 nucleotides to about 750 nucleotides, about 700 nucleotides to about 800 nucleotides, about 750 nucleotides to about 850 nucleotides, about 800 t nucleotides o about 900 nucleotides, about 850 nucleotides to about 950 nucleotides, about 900 nucleotides to about 1000 nucleotides, about 20 nucleotides to about 200 nucleotides, about 100 nucleotides to about 300 nucleotides, about 200 nucleotides to about 400 nucleotides, about 300 nucleotides to about 500 nucleotides, about 400 nucleotides to about 600, nucleotides about 500 nucleotides to about 700 nucleotides, about 600 nucleotides to about 800 nucleotides, about 700 nucleotides to about 900 nucleotides, about 800 nucleotides to about 1000 nucleotides, about 20 nucleotides to about 250 nucleotides, about 100 nucleotides to about 400 nucleotides, about 200 nucleotides to about 500 nucleotides, about 300 nucleotides to about 600 nucleotides, about 400 nucleotides to about 700 nucleotides, about 500 nucleotides to about 800 nucleotides, about 600 nucleotides to about 900 nucleotides, about 700 nucleotides to about 1000 nucleotides, about 20 nucleotides to about 300 nucleotides, about 150 nucleotides to about 500 nucleotides, about 250 nucleotides to about 600 nucleotides, about 400 nucleotides to about 800 nucleotides, about 600 nucleotides to about 1000 nucleotides, about 20 nucleotides to about 500 nucleotides, about 250 nucleotides to about 750 nucleotides, or about 500 nucleotides to about 1000 nucleotides, about 1000 nucleotides to about 1500 nucleotides, or about 1500 nucleotides to about 2000 nucleotides, or longer.

In some embodiments, the first polynucleotide sequence to which the first oligonucleotide binds is at the 3' end of the template polynucleotide or to the 3' end of its complement, such as the 3' end of a complementary extension product thereof. In certain embodiments, the first oligonucleotide binds to a 3' adapter. In one embodiment, the adapter is ligated to the 3' end of the template polynucleotide or to the 3' end of its complement, such as the 3' end of a complementary extension product thereof. In another embodiment, a template switching oligonucleotide (TSO) binds (e.g., hybridizes) to untemplated nucleotides that are added to the 3' end of the template polynucleotide or to the 3' end of its complement, such as the 3' end of a complementary extension product thereof. The 3' end of the TSO is then extended to generate an adapter that is complementary to the TSO. The untemplated nucleotides may be A, T, C, and/or G nucleotides, or any sequence thereof. In some embodiments, the untemplated nucleotides are a poly(C) or poly(G) sequence. In one embodiment, the untemplated nucleotides are a poly(C) sequence and the TSO includes a 3' poly(G) sequence. In another embodiment, the untemplated nucleotides are a poly(G) sequence and the TSO includes a 3' poly(C) sequence.

In some embodiments, the sequence of the first and/or second oligonucleotide may be about 10 nucleotides to about 50 nucleotides, about 10 nucleotides to about 20 nucleotides, about nucleotides to about 20 nucleotides, about 20 nucleotides to about 30 nucleotides, about 25 nucleotides to about 35 nucleotides about 30 nucleotides to about 40 nucleotides, or about 35 nucleotides to about 45 nucleotides, or about 40 nucleotides to about 50 nucleotides, about 10 nucleotides to about 30 nucleotides, about 15 nucleotides to about 35 nucleotides, about 20 to about 40 nucleotides, about 25 nucleotides to about 45 nucleotides, about 30 nucleotides to about 50 nucleotides in length, or any of about 10, 15, 20, 25, 30, 35, 40, 45, or 50 nucleotides in length.

In some embodiments, the second and/or third sequence to which a 5' or 3' sequence of the second oligonucleotide, respectively, binds may be about 10 nucleotides to about 50 nucleotides, about 10 nucleotides to about 20 nucleotides, about 15 nucleotides to about 20 nucleotides, about 20 nucleotides to about 30 nucleotides, about 25 nucleotides to about 35 nucleotides about 30 nucleotides to about 40 nucleotides, or about 35 nucleotides to about 45 nucleotides, or about 40 nucleotides to about 50 nucleotides, about 10 nucleotides to about 30 nucleotides, about 15 nucleotides to about 35 nucleotides, about 20 to about 40 nucleotides, about 25 nucleotides to about 45 nucleotides, about 30 nucleotides to about 50 nucleotides in length, or any of about 10, 15, 20, 25, 30, 35, 40, 45, or 50 nucleotides in length.

In some embodiments, the second oligonucleotide includes a linker, e.g., between the sequences that are complementary to the second and third sequences of the template polynucleotide or a complement thereof, such as a complementary extension product thereof. The linker may be a sequence of nucleotides that is not complementary to a sequence of the template polynucleotide or a complement thereof, such as a complementary extension product thereof. In a nonlimiting embodiment, the linker includes the sequence (AT)n. In some embodiments, the linker is about 1 nucleotide to about 50 nucleotides, about 1 nucleotide to about 5 nucleotides, about 1 nucleotide to about 10 nucleotides, about 5 nucleotides to about 10 nucleotides, about 10 nucleotides to about 20 nucleotides, about 15 nucleotides to about 20 nucleotides, about 20 nucleotides to about 30 nucleotides, about 25 nucleotides to about 35 nucleotides about 30 nucleotides to about 40 nucleotides, or about 35 nucleotides to about 45 nucleotides, or about 40 nucleotides to about 50 nucleotides, about 10 nucleotides to about 30 nucleotides, about 15 nucleotides to about 35 nucleotides, about 20 to about 40 nucleotides, about 25 nucleotides to about 45 nucleotides, about 30 nucleotides to about 50 nucleotides in length, or any of about 1, 5, 10, 15, 20, 25, 30, 35, 40, 45, or 50 nucleotides in length.

The polynucleotide product after oligonucleotide extension may be used for amplification and/or sequencing, for example, to detect presence and/or quantity of a template polynucleotide, and/or determine a 5' and/or 3' sequence of the template polynucleotide or a complement thereof, and/or to determine location (e.g., spatial location) of the biological analyte or a polynucleotide sequence thereof.

In some embodiments of the method, the template polynucleotide may be immobilized on a substrate (support or surface). For example, the template polynucleotide may be bound (e.g., hybridized) to a capture domain of a probe. In some embodiments, the probe may be configured as a component of an array of probes on the support. The array may be, for example, a bead array or a slide. For example, the probe may be attached to a feature in an array. The probe may be attached directly or indirectly to the substrate. In some embodiments, the probe is attached indirectly to the substrate, such as attached to beads (for example, gel beads) that are attached to the substrate. In some embodiments, the probe is attached indirectly to the substrate via a linker (for example, a photocleavable, chemically cleavable, or enzymatically cleavable linker) that are attached to the substrate.

In some instances, the first capture domain includes a poly-T sequence. In some instances, the capture domain includes a sequence complementary to a region of an immune molecule, such as the constant region of a TCR or BCR sequence (as described herein). In some instances, the capture domain includes a sequence complementary to a region of an immunoglobulin molecule, such as one or more CDRs of an immunoglobulin heavy or light chain. In some embodiments, the template polynucleotide includes a genetic variation, such as an isoform, a splice variant, or a single nucleotide polymorphism (SNP), e.g., in a 5' region of the mRNA, and the method includes detection and/or sequencing of the genetic variation. For example, the capture domain may include a sequence that is specific for the genetic variation, such as a sequence that binds to a change in a nucleic acid or protein (e.g., a mutation or SNP).

The biological sample from which the template polynucleotide is derived may be, for example, a tissue section, a primary cell, a cell line, or an organoid. In some embodiments, the method includes permeabilizing the biological sample, to release a biological analyte, prior to binding of the first and second oligonucleotides to the template polynucleotide of the biological analyte, for example, prior to contacting a capture probe with the template polynucleotide of the biological analyte. In some embodiments, the biological sample is a tissue section, such as a fixed (e.g., formalin-fixed and paraffin-embedded (FFPE) or paraformaldehyde (PFA)) tissue section, or a fresh frozen tissue section.

Figure 6:
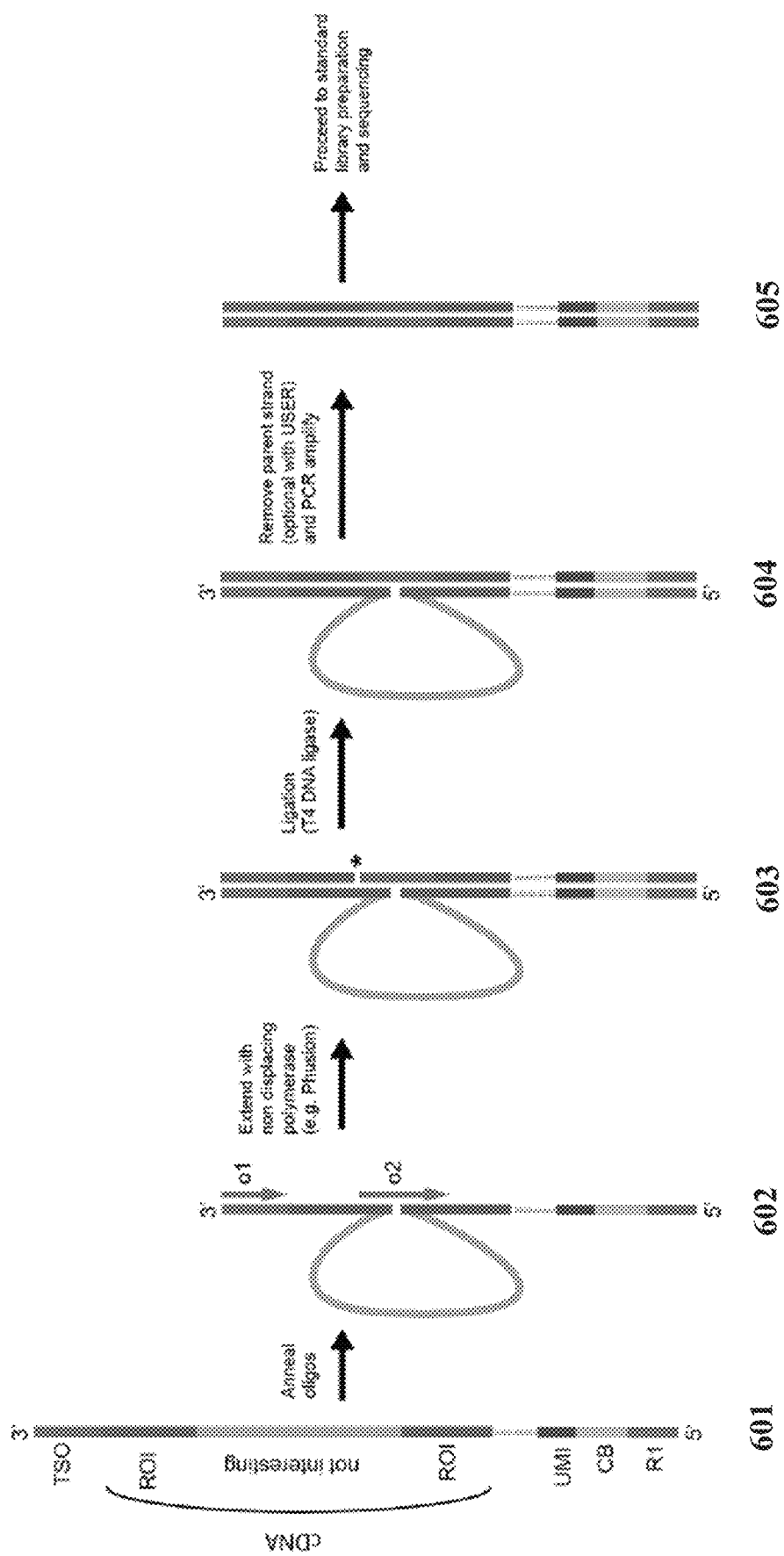
FIG. 6 depicts an exemplary workflow for processing of a template polynucleotide to remove a sequence that is not of interest for detection and/or analysis.

An exemplary, non-limiting workflow is depicted in FIG. 6. A cDNA complement 601 of a template polynucleotide includes two regions of interest (ROI) flanking a region that is not of interest, and an adapter at the 3' end (TSO). First and second oligonucleotides (o1 and o2, respectively) are annealed to a first cDNA sequence and to second and third cDNA sequences, respectively, bridging and bringing the two ROIs into proximity (602). First and second oligonucleotides are extended with a polymerase. (603) Extension of the first oligonucleotide ceases when a 5' phosphate (*) of the second oligonucleotide is reached. The 3' end of the extended first oligonucleotide is ligated to the 5' end of the second oligonucleotide, resulting in a polynucleotide product that contains the sequences of the two ROIs and that does not contain the sequence of the region that is not of interest. (604) The polynucleotide product may be amplified (605), and optionally sequenced. In some embodiments, the cDNA 601 may be an extension product from a template polynucleotide bound to a capture domain of a capture probe, as described herein. In other embodiments, the template polynucleotide may be an analyte from a single cell, and may be converted to a cDNA molecule as described above (for example, but not limited to the workflow depicted in FIG. 5).

In some embodiments, the disclosure provides for kits for capturing and determining the location and abundance of analytes from a biological sample as described herein. A kit would include, for example, an array comprising a first and second oligonucleotide probe reversibly affixed to the array, enzymes for practicing the methods such as a ligase as described herein, a terminal transferase as described herein, a polymerase as described herein, cleavage enzymes as described herein, library preparatory reagents as described herein, and buffers and dNTPs for practicing the different steps in the methods for capturing and determining the location of a nucleic acid of interest from the biological sample. Further, a kit can include instructions that would provide a user with details on how to practice one or more of the methods for capturing and determining the location of a nucleic acid of interest from a biological sample.

What is claimed is:

1. A method for determining a location of a target analyte within a biological sample, the method comprising:
   (a) contacting the biological sample with a substrate comprising a probe, wherein:
   the probe comprises, in a 5' to 3' direction: a spatial barcode sequence and a capture domain,
   wherein the target analyte in the biological sample hybridizes to the capture domain;
   (b) extending a 3' end of the probe to generate an extension product that comprises a nucleotide sequence complementary to the target analyte, or a portion thereof;
   (c) hybridizing a first and a second oligonucleotide to the extension product, wherein:
   the first oligonucleotide comprises a sequence that is complementary to a first sequence of the extension product;
   the second oligonucleotide comprises: a sequence that is complementary to a first flanking sequence and a second flanking sequence of the extension product, wherein the first and second flanking sequences are 3' and 5', respectively, of a portion to be removed from the extension product thereby bringing the first and second flanking regions adjacent for removal of a portion of the extension product,
   (d) extending the first and second oligonucleotides, wherein extension of the first oligonucleotide ceases when the second oligonucleotide is reached, thereby resulting in a nick between the extended first and second oligonucleotides;
   (e) ligating the 3' end of the extended first oligonucleotide to a 5' end of the extended second oligonucleotide, thereby producing a polynucleotide product that lacks a region of the extended product,
   (f) releasing the ligated product from the extension product, and
   (g) determining (i) the spatial barcode sequence, or a complement thereof, and (ii) all or a portion of the sequence of the target analyte, or a complement thereof, and using the sequences of (i) and (ii) to determine the location of the target analyte within the biological sample.

2. The method of claim 1, wherein the first sequence of the extension product to which the first oligonucleotide hybridizes is at the 3' end of the extension product.

3. The method of claim 1, wherein step (b) comprises adding untemplated nucleotides to the 3' end of the extension product, hybridizing a template switching oligonucleotide to the untemplated nucleotides, and extending the 3' end of the extension product, thereby generating an adapter, wherein the adapter is complementary to the sequence of the template switching oligonucleotide.

4. The method of claim 3, wherein step (b) further comprises ligating the adapter to the 3' end of the extension product.

5. The method of claim 3, wherein the untemplated nucleotides comprise a poly(C) or poly(G) sequence.

6. The method of claim 1, wherein step (d) comprises extending the 3' ends of the first and second oligonucleotides with a non-strand displacing, non 5'-3' exonuclease DNA polymerase, and wherein step (e) comprises ligation with a DNA ligase.

7. The method of claim 1, wherein the probe is attached to the substrate by one or more uracils and prior to step (f) the probe is released from the substrate by digestion with an uracil excision reagent.

8. The method of claim 1, wherein the second oligonucleotide further comprises a linker between the sequences that are complementary to the first flanking sequence and the second flanking sequence of the extension product.

9. The method of claim 8, wherein the linker is about 1 to about 50 nucleotides in length and comprises the sequence (AT)n.

10. The method of claim 1, wherein the spatial barcode is 5' to the capture domain and the probe further comprises a unique molecular identifier.

11. The method of claim 1, wherein the biological sample is a tissue section.

12. The method of claim 11, wherein the tissue section is a formalin-fixed and paraffin-embedded (FFPE) tissue section or a fresh frozen tissue section.

13. The method of claim 1, wherein the target analyte is mRNA, and the mRNA encodes a T-cell receptor, a B-cell receptor, or an immunoglobulin heavy or light chain.

14. The method of claim 1 further comprising, after step (f): generating an amplification product from the ligation product.

15. The method of claim 1, wherein the first and second oligonucleotides are about 10 to about 50 nucleotides in length.

16. The method of claim 1, wherein step (a) further comprises permeabilizing the biological sample.

17. The method of claim 1, wherein the capture domain comprises a poly(T) sequence, a random sequence, or a sequence that is complementary to the target analyte of interest.

18. The method of claim 1, wherein the substrate is a bead array or a slide.

19. The method of claim 1, wherein the target analyte is mRNA.

20. The method of claim 19, wherein the mRNA encodes a T-cell receptor or B-cell receptor.

* * * * *

SEQUENCE LISTING

<160> NUMBER OF SEQ ID NOS: 8

<210> SEQ ID NO 1
<211> LENGTH: 9
<212> TYPE: DNA
<213> ORGANISM: Artificial Sequence
<220> FEATURE:
<223> OTHER INFORMATION: Sequence present within first Probe

<400> SEQUENCE: 1 tttttttt                                                                9

```
<210> SEQ ID NO 2
<211> LENGTH: 9
<212> TYPE: PRT
<213> ORGANISM: Artificial Sequence
<220> FEATURE:
<223> OTHER INFORMATION: Sequence present within second probe

<400> SEQUENCE: 2

Gly Gly Ile Gly Gly Ile Gly Gly Ile
1               5

<210> SEQ ID NO 3
<211> LENGTH: 16
<212> TYPE: DNA
<213> ORGANISM: Artificial Sequence
<220> FEATURE:
<223> OTHER INFORMATION: Sequence present within captured nucleic acid

<400> SEQUENCE: 3
aaaaaaaaaa aaaaaa                                                  16

<210> SEQ ID NO 4
<211> LENGTH: 12
<212> TYPE: DNA
<213> ORGANISM: Artificial Sequence
<220> FEATURE:
<223> OTHER INFORMATION: Sequence present within extended first probe

<400> SEQUENCE: 4
cccccccccc cc                                                      12

<210> SEQ ID NO 5
<211> LENGTH: 17
<212> TYPE: DNA
<213> ORGANISM: Artificial Sequence
<220> FEATURE:
<223> OTHER INFORMATION: Sequence present within an extended first probe

<400> SEQUENCE: 5
cccccccccc ccccccc                                                 17

<210> SEQ ID NO 6
<211> LENGTH: 11
<212> TYPE: DNA
<213> ORGANISM: Artificial Sequence
<220> FEATURE:
<223> OTHER INFORMATION: Sequence present within captured nucleic acid

<400> SEQUENCE: 6
aaaaaaaaaa a                                                       11

<210> SEQ ID NO 7
<211> LENGTH: 9
<212> TYPE: DNA
<213> ORGANISM: Artificial Sequence
<220> FEATURE:
<223> OTHER INFORMATION: Sequence present within extended probe

<400> SEQUENCE: 7 ttttttttt                                                           9

<210> SEQ ID NO 8
<211> LENGTH: 9
<212> TYPE: DNA
<213> ORGANISM: Artificial Sequence
```

```
<220> FEATURE:
<223> OTHER INFORMATION: Sequence present within a nucleic acid
      complementary to extended probe

<400> SEQUENCE: 8 aaaaaaaaa                                                              9
```